United States Patent
Kato et al.

[11] Patent Number: 5,173,493
[45] Date of Patent: * Dec. 22, 1992

[54] PYRIDOINDOLE DERIVATIVES AND PROCESSES FOR PREPARATION THEREOF

[75] Inventors: Masayuki Kato, Kyoto; Kiyotaka Ito, Ikeda; Hisashi Takasugi, Osaka, all of Japan

[73] Assignee: Fujisawa Pharmaceutical Company, Ltd., Osaka, Japan

[*] Notice: The portion of the term of this patent subsequent to Aug. 25, 2009 has been disclaimed.

[21] Appl. No.: 495,119

[22] Filed: Mar. 19, 1990

Related U.S. Application Data

[63] Continuation-in-part of Ser. No. 409,744, Sep. 20, 1989.

[30] Foreign Application Priority Data

Sep. 27, 1988 [GB] United Kingdom ................ 8822646
Feb. 10, 1989 [GB] United Kingdom ................ 8903044

[51] Int. Cl.$^5$ .................... A61K 31/44; C07D 459/00
[52] U.S. Cl. .................................. 514/294; 546/94; 546/95; 546/96
[58] Field of Search ................ 546/94, 95, 96; 514/294

[56] References Cited

U.S. PATENT DOCUMENTS 4,963,546 10/1990 North et al. ........................ 546/94

Primary Examiner—C. Warren Ivy
Assistant Examiner—Celia Chang
Attorney, Agent, or Firm—Oblon, Spivak, McClelland, Maier & Neustadt

[57] ABSTRACT

The invention relates to compounds for treatment of nausea and vomiting, of the formula

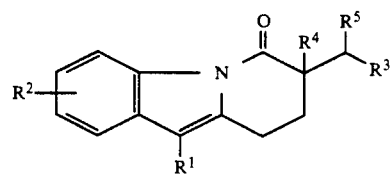

wherein
$R^1$ is hydrogen, lower alkyl, lower alkenyl or N,N-di(-lower)alkylaminomethyl,
$R^2$ is hydrogen, lower alkyl or halogen,
$R^3$ is imidazolyl or pyridyl, each of which may have substituent(s) selected from lower alkyl and iminoprotective group, and
$R^4$ is hydrogen, lower alkyl, lower alkenyl or hydroxy(-lower)alkyl and $R^5$ is hydrogen, hydroxy or lower alkanoyloxy, or
$R^4$ and $R^5$ are linked together to form an additional bond,
or a pharmaceutically acceptable salt thereof.

9 Claims, No Drawings

PYRIDOINDOLE DERIVATIVES AND PROCESSES FOR PREPARATION THEREOF

This application is a continuation in part of U.S. application Ser. No. 07/409,744 filed Sep. 20, 1989.

The present invention relates to novel pyridoindole derivatives and a pharmaceutically acceptable salt thereof. More particularly, it relates to novel pyridoindole derivatives and a pharmaceutically acceptable salt thereof which have pharmacological activities such as 5-hydroxytryptamine (5-HT) antagonism and the like, to processes for preparation thereof, to a pharmaceutical composition comprising the same and to a use of the same as a medicament.

Accordingly, one object of the present invention is to provide novel pyridoindole derivatives and a pharmaceutically acceptable salt thereof, which are useful as a potent and selective antagonist of 5-HT receptor.

Another object of the present invention is to provide processes for preparation of said pyridoindole derivatives or a salt thereof.

A further object of the present invention is to provide a pharmaceutical composition comprising, as an active ingredient, said pyridoindole derivatives or a pharmaceutically acceptable salt thereof.

Still further object of the present invention is to provide a use of said pyridoindole derivatives or a pharmaceutically acceptable salt thereof as a 5-HT antagonist useful for treating or preventing central nervous system (CNS) disorders such as psychosis (e.g. schizophrenia, mania, etc.), anxiety, and depression; pains or aches such as headaches (e.g. migraine, cluster headaches, vascular headaches, etc.) and neuralgia (e.g. trigeminal neuralgia, etc.); gastrointestinal disorders such as symptoms of gastrointestinal dysfunction such as occur with, for example, dyspepsia, peptic ulcer, reflux oesophagitis and flatulence, and irritable bowel syndrome (IBS); nausea or vomiting, each of which may be associated with cancer therapy; motion sickness; and the like in human being or animals, particularly nausea and vomiting.

With regard to the states of the arts in this field, for example, the following compound is known.

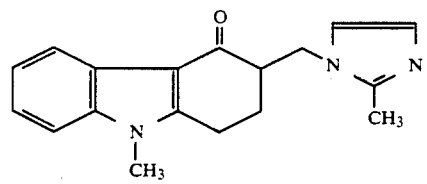

(Japanese Patent Gazette KOKAI 60-214784)

As a result of an extensive study, the inventors of the present invention could obtain the pyridoindole derivatives which have strong pharmacological activities.

The pyridoindole derivatives of the present invention are novel and can be represented by the formula (I):

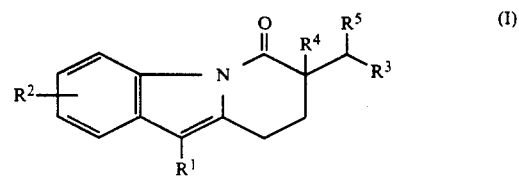

wherein
$R^1$ is hydrogen, lower alkyl, lower alkenyl or N,N-di(-lower)alkylaminomethyl,
$R^2$ is hydrogen, lower alkyl or halogen,
$R^3$ is imidazolyl or pyridyl, each of which may have suitable substituent(s), and
$R^4$ is hydrogen, lower alkyl, lower alkenyl or hydroxy(-lower)alkyl and
$R^5$ is hydrogen, hydroxy or acyloxy, or
$R^4$ and $R^5$ are linked together to form an additional bond.

With regard to the compound (I) of the present invention, it is to be noted that there may be one or more optically isomeric pairs due to the presence of one or more asymmetric carbon atom(s) and these isomers or a mixture thereof are included within a scope of the compound (I) of the present invention.

According to the present invention, the object compound (I) can be prepared by the following processes:

Process 1

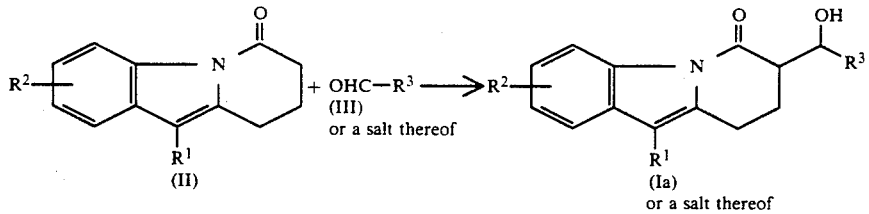

Process 2:

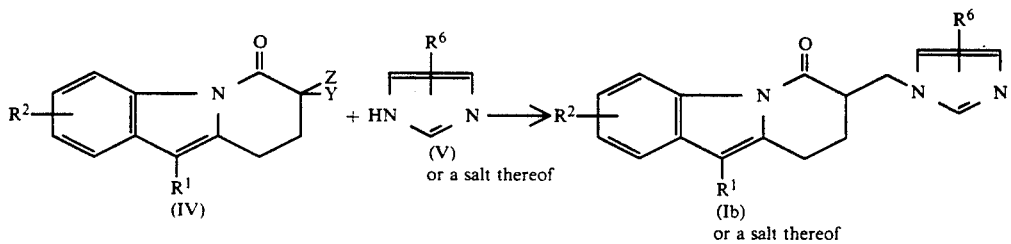

Process 3:

-continued

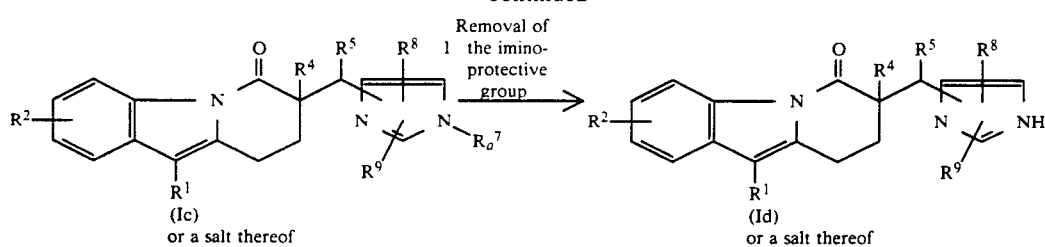

(Ic) or a salt thereof  →  Removal of the imino-protective group  →  (Id) or a salt thereof Process 4:

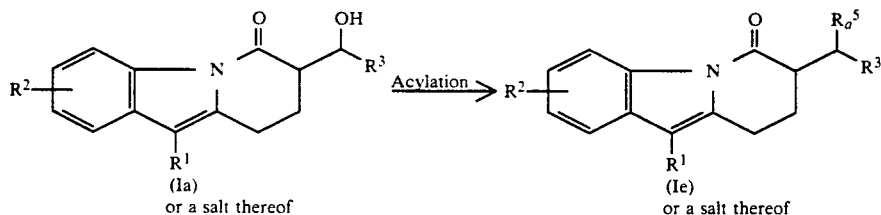

(Ia) or a salt thereof  →  Acylation  →  (Ie) or a salt thereof

Process 5:

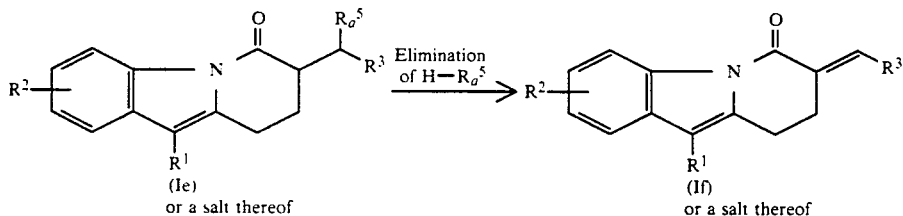

(Ie) or a salt thereof  →  Elimination of H—$R_a^5$  →  (If) or a salt thereof

Process 6:

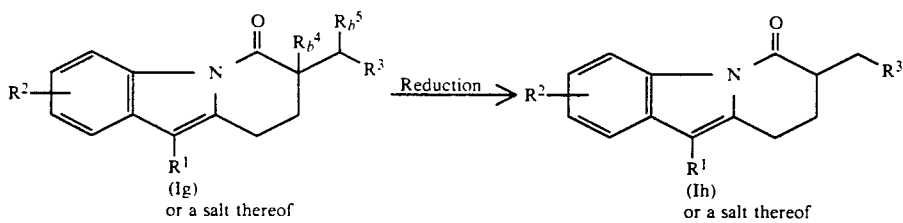

(Ig) or a salt thereof  →  Reduction  →  (Ih) or a salt thereof

Process 7:

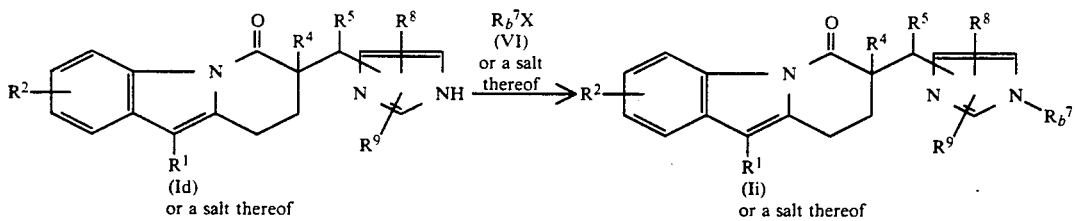

(Id) or a salt thereof  →  $R_b^7X$ (VI) or a salt thereof  →  (Ii) or a salt thereof Process 8:

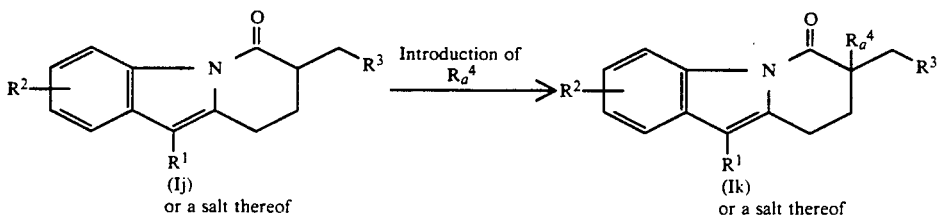

(Ij) or a salt thereof  →  Introduction of $R_a^4$  →  (Ik) or a salt thereof

Process 9:

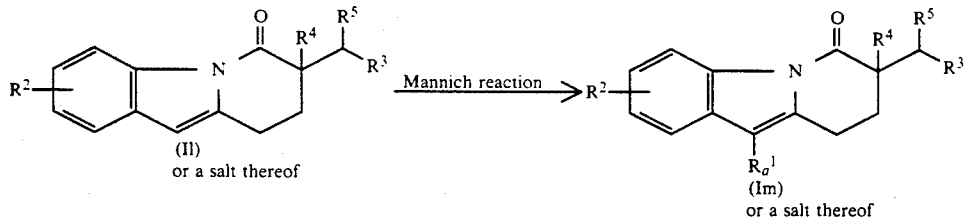

(II) or a salt thereof → Mannich reaction → (Im) or a salt thereof

Process 10:

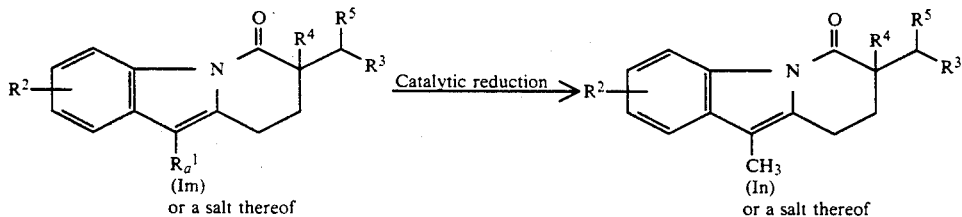

(Im) or a salt thereof → Catalytic reduction → (In) or a salt thereof

Suitable salt of the compounds (I), (Ia), (Ib), (Ic), (Id), (Ie), (If), (Ig), (Ih), (Ii), (Ij), (Ik), (Il), (Im), (In), (Io), (Ip), (III), (V) and (VI) are conventional non-toxic, pharmaceutically acceptable salt and may include a salt with a base or an acid addition salt such as a salt with an inorganic base, for example, an alkali metal salt (e.g. sodium salt, potassium salt, cesium salt, etc.), an alkaline earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N'-dibenzylethylenediamine salt, etc.), etc.; an inorganic acid addition salt (e.g. hydrochloride, hydrobromide, sulfate, phosphate, etc.); an organic carboxylic or sulfonic acid addition salt (e.g. formate, acetate, trifluoroacetate, maleate, tartrate, methanesulfonate, benzenesulfonate, p-toluenesulfonate, etc.); a salt with a basic or acidic amino acid (e.g. arginine, aspartic acid, glutamic acid, etc.); and the like, and the preferable example thereof is an acid addition salt.

In the above and subsequent descriptions of the present specification, suitable examples and illustrations of the various definitions which the present invention include within the scope thereof are explained in detail as follows.

The term "lower" is intended to mean 1 to 6 carbon atoms, preferably 1 to 4 carbon atoms, unless otherwise indicated.

Suitable "lower alkyl" may include straight or branched one, having 1 to 6 carbon atom(s), such as methyl, ethyl, propyl, isopropyl, butyl, t-butyl, pentyl, hexyl, preferably one having 1 to 4 carbon atoms, and the like, in which the most preferred one is methyl, ethyl or propyl.

Suitable "lower alkenyl" may include vinyl, 1-propenyl, allyl, 1-butenyl, 2-butenyl, 2-pentenyl, and the like, preferably one having 2 to 4 carbon atoms, in which the most preferred one is allyl.

Suitable "hydroxy(lower)alkyl" is lower alkyl as mentioned above which is substituted by hydroxy and may include hydroxymethyl, hydroxyethyl, hydroxypropyl, and the like, in which the most preferred one is hydroxymethyl.

Suitable "halogen" means fluoro, chloro, bromo and iodo, in which the most preferred one is chloro.

Suitable "imidazolyl" means 1H-imidazolyl-1-yl, 1H-imidazol-2-yl, 1H-imidazol-4-yl and 1H-imidazol-5-yl.

Suitable "pyridyl" means 2-pyridyl, 3-pyridyl and 4-pyridyl.

Suitable substituent in the terms "imidazolyl or pyridyl, each of which may have suitable substituent(s)" is conventional one used in a pharmaceutical field and may include lower alkyl as mentioned above, imino-protective group as mentioned below, and the like.

Suitable acyl moiety in the term "acyloxy" may include conventional one derived, for example, from carboxylic, carbonic, sulfonic and carbamic acids, and the preferable example thereof is lower alkanoyl (e.g. formyl, acetyl, propionyl, butyryl, isobutyryl, valeryl, isovaleryl, pivaloyl, hexanoyl, etc.), lower alkanesulfonyl (e.g. mesyl, ethanesulfonyl, propanesulfonyl, etc.), and the like, in which the most preferred one is acetyl.

These acyl group may be substituted with suitable substituent(s) such as halogen (e.g. chlorine, bromine, iodine, fluorine).

Suitable "imino-protective group" may include conventional one, and the preferable example thereof is ar(lower)alkyl such as mono-(or di- or tri-)phenyl(lower)alkyl (e.g. benzyl, benzhydryl, trityl, etc.), acyl such as N,N-di(lower)alkylsulfamoyl (e.g. N,N-dimethylsulfamoyl, etc.), lower alkanesulfonyl (e.g. mesyl, etc.), arenesulfonyl (e.g. tosyl, etc.), and the like, in which the most preferred one is trityl, benzyl or N,N-dimethylsulfamoyl.

Suitable "acid residue" may include halogen as mentioned above, and the like.

Suitable "N,N-di(lower)alkylaminomethyl" may include N,N-dimethylaminomethyl, and the like.

Particularly, the preferred embodiments of $R^1$, $R^2$, $R^3$, $R^4$ and $R^5$ are as follows.

$R^1$ is hydrogen; lower alkyl such as methyl, ethyl, propyl, etc.; lower alkenyl such as allyl, etc.; or N,N-di(lower)alkylaminomethyl such as N,N-dimethylaminomethyl, etc.;

$R^2$ is hydrogen; lower alkyl such as methyl, etc.; or halogen such as chloro;

$R^3$ is 1H-imidazolyl which may have one or more, preferably one to three substituent(s) selected from lower alkyl and imino-protective group such as 2-lower alkyl-1H-imidazol-1-yl (e.g. 2-methyl-1H-imidazol-1-yl, etc.), 1H-imidazol-2-yl, 1-ar(lower)alkyl-1H-imidazol-2-yl (e.g. 1-trityl-1H-imidazol-2-yl, etc.), 1-ar(lower)alkyl-5-lower alkyl-1H-imidazol-4-yl (e.g. 5-methyl-1-trityl-1H-imidazol-4-yl, 1-benzyl-5-methyl-1H-imidazol-4-yl, etc.), 5-lower alkyl-1H-imidazol-4-yl (e.g. 5-methyl-1H-imidazol-4-yl, etc.), 1-ar(lower)alkyl-1H-imidazol-4-yl (e.g. 1-trityl-1H-imidazol-4-yl, etc.), 1H-imidazol-4-yl, 2-lower alkyl-5-lower alkyl-1H-imidazol-4-yl (e.g. 2,5-dimethyl-1H-imidazol-4-yl, etc.), 1-ar(lower)alkyl-2-lower alkyl-1H-imidazol-4-yl (e.g. 2-methyl-1-trityl-imidazol-4-yl, etc.), 2-lower alkyl-1H-imidazol-4-yl (e.g. 2-methyl-1H-imidazol-4-yl, etc.), 1-lower alkyl-1H-imidazol-4-yl (e.g. 1-methyl-1H-imidazol-4-yl, etc.), 1-lower alkyl-5-lower alkyl-1H-imidazol-4-yl (e.g. 1,5-dimethyl-1H-imidazol-4-yl, etc.) and 1-di(lower)alkylaminosulfonyl-5-lower alkyl-1H-imidazol-4-yl (e.g. 1-dimethylaminosulfonyl-5-methyl-1H-imidazol-4-yl, etc.), 1-lower alkyl-1H-imidazol-5-yl (e.g. 1-methyl-1H-imidazol-5-yl, etc.) and 1-lower alkyl-4-lower alkyl-1H-imidazol-5-yl (e.g. 1,4-dimethyl-1H-imidazol-5-yl, etc.); pyridyl which may have lower alkyl such as 3-pyridyl which may have suitable substituent(s) such as 3-pyridyl and 2-lower alkyl-3-pyridyl (e.g. 2-methyl-3-pyridyl, etc.); and $R^4$ is hydrogen; lower alkyl such as methyl, ethyl, propyl, etc.; lower alkenyl such as allyl, etc.; or hydroxy(lower)alkyl such as hydroxymethyl, etc.; and $R^5$ is hydrogen; hydroxy; or acyloxy such as lower alkanoyloxy (e.g. acetoxy, etc.), and the like; or $R^4$ and $R^5$ are linked together to form an additional bond.

The processes 1 to 11 for preparing the object compound (I) of the present invention are explained in detail in the following.

Process 1:

The object compound (Ia) or a salt thereof can be prepared by reacting the compound (II) with the compound (III) or a salt thereof.

The present reaction is usually carried out in the presence of a base such as alkyl lithium (e.g. n-butyllithium, etc.), alkali metal hydride (e.g. sodium hydride, potassium hydride, etc), and the like.

The present reaction is usually carried out in a solvent such as dioxane, dimethylsulfoxide, dimethylformamide, diethylformamide, dimethylacetamide, benzene, hexane, tetrahydrofuran, or any other solvent which does not adversely affect the reaction.

The reaction temperature is not critical and the reaction is usually carried out under cooling, at ambient temperature or under heating.

Process 2:

The object compound (Ib) or a salt thereof can be prepared by reacting the compound (IV) with the compound (V) or a salt thereof.

The reaction is usually carried out in a solvent such as water, alcohol [e.g. methanol, ethanol, propanol, etc.], acetic acid, diethyl ether, dioxane, tetrahydrofuran, methylene chloride, chloroform, N,N-dimethylformamide, dimethylsulfoxide, or any other organic solvent which does not adversely influence the reaction, or a mixture thereof.

The reaction temperature is not critical and the reaction is usually carried out at ambient temperature, under warming or under heating.

Process 3:

The object compound (Id) or a salt thereof can be prepared by subjecting the compound (Ic) or a salt thereof to removal reaction of the imino-protective group.

Suitable method for this removal may include conventional one such as hydrolysis, reduction, or the like. The hydrolysis is preferably carried out in the presence of the base or an acid.

Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate, (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as trialkylamine (e.g. trimethylamine, triethylamine, etc.), picoline, N-methylpyrrolidine, N-methylmorpholine, 1,5-diazabicyclo[4,3,0]non-5-one, 1,4-diazabicyclo[2,2,2]octane, 1,5-diazabicyclo[5,4,0]undecene-5 or the like. The hydrolysis using a base is often carried out in water or a hydrophilic organic solvent or a mixed solvent thereof.

Suitable acid may include an organic acid (e.g. formic acid, acetic acid, propionic acid, etc.) and an inorganic acid (e.g. hydrochloric acid, hydrobromic acid, sulfuric acid, etc.).

The present hydrolysis is usually carried out in an organic solvent, water or a mixed solvent thereof.

The reaction temperature is not critical, and the reaction is usually carried out at ambient temperature or under warming or heating.

The reduction may include catalytic reduction and chemical reduction as explained in Process 6 and can be carried out by a conventional method.

The method applied for this removal reaction can be selected depending on the kind of the imino-protective group.

The present removal reaction includes, within its scope, the case that hydroxy or acyloxy for $R^5$, or the additional bond formed by linkage of $R^4$ and $R^5$ is eliminated during the reaction or at the post-treating step of the present process.

In such cases, the reaction is preferably carried out in the presence of catalyst (e.g. palladium on carbon, etc.), ammonium formate and acetic acid under heating.

Process 4:

The object compound (Ie) or a salt thereof can be prepared by reacting the compound (Ia) or a salt thereof with an acylating agent.

The compound (Ia) may be used in the form of its conventional reactive derivative at the hydroxy group.

The acylating agent can be represented by the compound of the formula:

$$R_a^5\text{---H}$$

in which $R_a^5$ is acyloxy as defined above and its conventional reactive derivative at the hydroxy group.

The suitable example may be an acid halide (e.g. acid chloride, etc.), an acid anhydride, (e.g. acetic anhydride, etc.), an activated amide, an activated ester, and the like.

The reaction is usually carried out in a conventional solvent such as water, acetone, dioxane, acetonitrile, chloroform, dichloromethane, ethylene chloride, tetrahydrofuran, ethyl acetate, N,N-dimethylformamide, N,N-dimethylacetamide, pyridine or any other organic solvent which does not adversely influence the reaction. These conventional solvents may also be used in a mixture with water.

The reaction temperature is not critical, and the reaction is usually carried out under cooling to warming.

The reaction may also be carried out in the presence of an inorganic or organic base such as an alkali metal bicarbonate, tri(lower)alkylamine, pyridine, N-(lower)alkylmorphorine, N,N-di(lower)alkylbenzylamine, and the like.

Process 5:

The object compound (If) or a salt thereof can be prepared by subjecting the compound (Ie) or a salt thereof to elimination reaction of $HR_a{}^5$ group.

The elimination reaction can usually be carried out by an inorganic base such as alkali metal hydride (e.g. sodium hydride, potassium hydride, etc.), or the like, and an organic base such as trialkylamine (e.g. trimethylamine, triethylamine, etc.), picoline, N-methylpyrrolidine, N-methylmorpholine, 1,5-diazabicyclo[4.3.0]-non-5-ene, 1,4-diazabicyclo[2.2.2]octane, 1,8-diazabicyclo[5.4.0]undec-7-ene, or the like.

The present reaction is usually carried out in a solvent such as dioxane, dimethyl sulfoxide, dimethylformamide, diethylformamide, dimethylacetamide, benzene, tetrahydrofuran, toluene, or any other solvent which does not adversely affect the reaction.

The reaction temperature is not critical and the reaction is usually carried out under cooling, at ambient temperature or under heating.

Process 6:

The object compound (Ih) or a salt thereof can be prepared by subjecting the compound (Ig) or a salt thereof to reduction reaction.

The reaction can be carried out in a conventional manner, for example, chemical reduction or catalytic reduction.

Suitable reducing agents to be used in chemical reduction are a metal hydride compound such as aluminum hydride compound [e.g. lithium aluminum hydride, sodium aluminum hydride, aluminum hydride, lithium trimethoxyaluminum hydride, lithium tri-t-butoxyaluminum hydride, etc.], borohydride compound [e.g. sodium borohydride, lithium borohydride, sodium cyanoborohydride, tetramethylammonium borohydride, etc.], borane, diborane, aluminum halide [e.g. aluminum chloride, etc.], phosphorus trihalide [e.g. phosphorus trichloride, phosphorus tribromide, etc.], ferrous oxalate, a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.] or the like.

Suitable catalysts to be used in catalytic reduction are conventional ones such as platinum catalyst [e.g. platinum plate, spongy platinum, platinum black, colloidal platinum, platinum oxide, platinum wire, etc.], palladium catalyst [e.g. spongy palladium, palladium black, palladium oxide, palladium on carbon, colloidal palladium, palladium on barium sulfate, palladium on barium carbonate etc.], nickel catalyst [e.g. reduced nickel, nickel oxide, Raney nikel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.] or the like.

The preferable manner is catalytic reduction.

The reaction is usually carried out in a solvent such as water, alcohol [e.g. methanol, ethanol, propanol, etc.], acetic acid, diethyl ether, dioxane, tetrahydrofuran, methylene chloride, chloroform, N,N-dimethylformamide, dimethylsulfoxide, or any other organic solvent which odes not adversely influence the reaction, or a mixture thereof.

The reaction is preferably carried out in the presence of ammonium formate.

The reaction is preferably carried out under somewhat milder conditions such as under cooling to warming.

The present reaction includes, within its scope, the case that the imino-protective group on $R^3$ is eliminated during the reaction or at the post-treating step of the present process.

Process 7:

The object compound (Ii) or a salt thereof can be prepared by reacting the compound (Id) or a salt thereof with the compound (VI).

The present reaction is usually carried out in the presence of a base such as alkyl lithium (e.g. n-butyl lithium, etc.), alkali metal hydride (e.g. sodium hydride, potassium hydride, etc.), di(lower)alkylamine (e.g. diisopropylamine, etc.), tri(lower)alkylamine (e.g. trimethylamine, triethylamine, etc.), pyridine or its derivative (e.g. picoline, lutidine, 4-dimethylaminopyridine, etc.), or the like.

The present reaction is usually carried out in a solvent such as dioxane, dimethyl sulfoxide, dimethylformamide, diethylformamide, dimethylacetamide, benzene, tetrahydrofuran, or any other solvent which does not adversely affect the reaction. In case that the base to be used is liquid, it can also be used as a solvent.

The reaction temperature is not critical and the reaction is usually carried out under cooling, at ambient temperature or under heating.

Process 8:

The object compound (Ik) or a salt thereof can be prepared by subjecting the compound (Ij) or a salt thereof to introduction reaction of $R_a{}^4$.

In case that $R_a{}^4$ to be introduced is lower alkyl or lower alkenyl, the introducing agent of $R_a{}^4$ can be represented by the compound of the formula:

$$R_a{}^4 X^1$$

in which
$R_a{}^4$ is lower alkyl or lower alkenyl, and
$X^1$ is acid residue as defined above.

In case that $R_a{}^4$ to be introduced is hydroxy(lower)alkyl, the introducing agent of $R_a{}^4$ can be represented by the compound of the formula:

$$(R^{10}CHO)_n$$

in which
$R^{10}$ is hydrogen or lower alkyl, and
n is integer.

This reaction can be carried out in substantially the same manner as Process 7, and therefore the reaction mode and reaction conditions [e.g. solvents, bases, reaction temperature, etc.] of this reaction are to be referred to those as explained in Process 7.

Process 9:

The object compound (Im) or a salt thereof can be prepared by subjecting the compound (Il) or a salt thereof to Mannich reaction.

The reaction is carried out in the presence of formaldehyde and N,N-di(lower)alkylamine used in Mannich reaction.

The reaction is usually carried out in the presence of an organic acid (e.g. formic acid, acetic acid, propionic acid, etc.) and an inorganic acid (e.g. hydrochloric acid, hydrobromic acid, sulfuric acid, etc.).

The present reaction is usually carried out in a solvent such as dioxane, dimethyl sulfoxide, dimethylformamide, diethylformamide, dimethylacetamide, benzene, tetrahydrofuran, or any other solvent which does not adversely affect the reaction. In case that the acid to be used is liquid, it can also be used as a solvent.

The reaction temperature is not critical and the reaction is usually carried out under cooling, at ambient temperature or under heating.

Process 10:

The object compound (In) or a salt thereof can be prepared by subjecting the compound (Im) or a salt thereof to catalytic reduction reaction.

The reaction may be catalytic reduction as explained in Process 6, and therefore the reaction mode and reaction conditions [e.g. solvents, bases, reaction temperature, etc.] of this reaction are to be referred to those as explained in Process 6.

The present reaction includes, within its scope, the case that the imino-protective group on $R^3$ is eliminated during the reaction or at the post-treating step of the present process.

Process 11:

The object compound (Ip) or a salt thereof can be prepared by subjecting the compound (Io) or a salt thereof to reduction reaction.

This reaction can be carried out in substantially the same manner as Process 6, and therefore the reaction mode and reaction conditions [e.g. solvents, bases, reaction temperature, etc.] of this reaction are to be referred to those as explained in Process 6.

Among the starting compounds (II), (III), (IV), (V) and (VI), some of them are new and such compounds can be prepared by the methods of Preparations mentioned below.

The object compound (I) of the present invention can be isolated and purified in a conventional manner, for example, extraction, precipitation, fractional crystallization, recrystallization, chromatography, and the like.

The object compound (I) thus obtained can be converted to its salt by a conventional method.

The optically active isomers of the object compound (I) can be resolved by a conventional method such as a resolution by reacting a mixture of isomers with an optically active reagent. Such reagents include optically active acids (e.g., benzyloxycarbonyl-L-phenylalanine, di-p-toluoyltartaric acid, etc.) or acid derivatives such as acid chloride (e.g., l-menthoxyacetyl chloride, etc.) or acid anhydride, 2-pyrrolidinemethanol and the like.

The object compound (I) of the present invention are novel and exhibit pharmacological activities such as 5-HT antagonism, especially, $5\text{-HT}_3$ antagonism, and the like and therefore are useful as 5-HT antagonist for treating or preventing central nervous system (CNS) disorders such as psychosis (e.g. schizophrenia, mania, etc.), anxiety, and depression; pains or aches such as headaches (e.g. migraine, cluster headaches, vascular headaches, etc.), and neuralgia (e.g. trigeminal neuralgia, etc.); gastrointestinal disorders such as symptoms of gastrointestinal dysfunction such as occur with, for example, dyspepsia, peptic ulcer, reflux oesophagitis and flatulence, and irritable bowel syndrome (IBS); nausea or vomiting, each of which may be associated with cancer therapy; motion sickness; and the like.

Further, it is expected that the object compound (I) of the present invention are useful as therapeutical and/or preventive agents for obesity; lung embolism; arrhythmia; withdrawal syndrome resulting from addition to a drug or substance of abuse; stress-related psychiatric disorders; rhinitis; serotonin-induced nasal disorders; reperfusion injury; and dementia and other cognitive disorders, and the like.

In order to illustrate the usefulness of the object compounds (I), pharmacological activity of representative compound of the present invention are shown below.

[1] Test Compound

① 8,9-Dihydro-7-[(hydroxy)(5-methyl-1H-imidazol-4-yl)methyl]-10-methylpyrido[1,2-a]indol-6(7H)-one maleate (isomer B) (hereinafter referred to as Compound ①)

② 8,9-Dihydro-7-[(1H-imidazol-4-yl)methyl]-10-methylpyrido[1,2-a]indol-6(7H)-one (hereinafter referred to as Compound ②)

③ (+)-8,9-Dihydro-10-methyl-7-[(5-methyl-1H-imidazol-4-yl)methyl]pyrido[1,2-a]indol-6(7H)-one hydrochloride (hereinafter referred to as Compound ③)

④ 8,9-Dihydro-7,10-dimethyl-7-[(5-methyl-1H-imidazol-4-yl)methyl]pyrido[1,2-a]indol-6(7H)-one (hereinafter referred to as Compound ④)

[2] Test (A) Inhibition of Benzold-Jarisch reflex

Test Method:

Male Sprague-Dawley rats weighing 260–350 g were anesthetized intraperitoneally with 1.25 g/kg urethane.

Blood pressure and heart rate were monitored continuously from the left common carotid artery with a pressure transducer. A right femoral vein was connulated for the intravenous injection (iv) of drugs. The trachea was also connulated to ease the respiration.

Rats were given a rapid bolus injection of 2-methyl-5-hydroxytryptamine (32 μg/kg, iv) to establish the control bradycardic response. Once the heart rate returned to base line, the rats were given the test compound (iv), followed by 5-minutes interval and another bolus injection of 2-methyl-5-hydroxytryptamine (32 μg/kg, iv).

| Test Result: | |
|---|---|
| Compound | $ED_{50}$ (μ/kg) |
| ① | 5.9 |
| ② | 1.8 |
| ③ | 0.9 |
| ④ | 1.1 |

(B) Inhibition of Cisplatin-induced vomiting

Test Method:

Nonfasted female beagles weighing about 10 kg were administered test compound or saline intravenously twice 10 minutes prior to and 90 minutes after Cisplatin dosing (3.2 mg/kg, iv).

Cisplatin was dissolved in 0.9% warm saline with a final concentration of 3 mg/ml and used immediately. The beagles were observed for vomiting for up to 5 hours following Cisplatin administration.

| Test Result: | |
|---|---|
| Compound | ED$_{50}$ (μg/kg) |
| ③ | 1.1 |

For therapeutic or preventive administration, the object compound (I) of the present invention are used in the form of conventional pharmaceutical preparation which contains said compound as an active ingredient, in admixture with pharmaceutically acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade and the like.

If needed, there may be included in the above preparations auxiliary substances, stabilizing agents, wetting agents and other commonly used additives such as lactose, citric acid, tartaric acid, stearic acid, magnesium stearate, terra alba, sucrose, corn starch, talc, gelatin, agar, pectin, peanut oil, olive oil, cacao butter, ethylene glycol, and the like.

While the dosage of the compound (I) may vary from and also depend upon the age, conditions of the patient, a kind of diseases or conditions, a kind of the compound (I) to be applied, etc. In general amounts between 0.01 mg and about 500 mg or even more per day may be administered to a patient. An average single dose of about 0.05 mg, 0.1 mg, 0.25 mg, 0.5 mg, 1 mg, 20 mg, 50 mg, 100 mg of the object compound (I) of the present invention may be used in treating diseases.

The following Preparations and Examples are given for the purpose of illustrating the present invention.

PREPARATION 1

To a suspension of p-chlorophenylhydrazine hydrochloride (8.52 g) in toluene (100 ml) were added 2-methylcyclohexane-1,3-dione (5.0 g) and 40% sulfuric acid (40 ml), and the mixture was stirred at 80°-85° C. for 4 hours. After cooling, the organic layer was separated. The aqueous layer was extracted with toluene. The organic layers were combined and washed with aqueous sodium bicarbonate, water, and brine. After dried over sodium sulfate, the organic layer was evaporated. The residue was recrystallized from methanol to give 2-chloro-8,9-dihydro-10-methylpyrido[1,2-a]indol-6(7H)-one (14.63 g).

mp: 102°-103° C.

IR (Nujol): 1690, 1675, 1625 cm$^{-1}$

NMR (CDCl$_3$, δ): 2.08 (2H, quint, J=6 Hz), 2.12 (3H, s), 2.75 (2H, t, J=6 Hz), 2.88 (2H, t, J=6 Hz), 7.21 (1H, dd, J=8.5 Hz, J=2 Hz,), 7.35 (1H, d, J=2 Hz), 8.32 (1H, d, J=8.5 Hz)

PREPARATION 2

8,9-Dihydro-2,10-dimethylpyrido[1,2-a]indol-6(7H)-one was prepared in a similar manner to that of Preparation 1.

mp: 106°-107° C.

IR (Nujol): 1705, 1675, 1620 cm$^{-1}$

NMR (CDCl$_3$, δ): 2.06 (2H, quint, J=6 Hz), 2.15 (3H, s), 2.45 (3H, s), 2.74 (2H, t, J=6 Hz), 2.88 (2H, t, J=6 Hz), 7.10 (1H, d, J=8.5 Hz), 7.20 (1H, s), 8.29 (1H, d, J=8.5 Hz)

PREPARATION 3

To a solution of diisopropylamine (1.21 g) in tetrahydrofuran (15 ml) at −70° C. under a nitrogen atmosphere was added 1.64M n-butyllithium in hexane (7.3 ml). After being stirred at the same temperature for 20 minutes, the mixture was treated with a solution of 8,9-dihydro-10-methylpyrido[1,2-a]indol-6(7H)-one (1.99 g) in tetrahydrofuran (20 ml) over 5 minutes. The mixture was stirred at −70° C. for 30 minutes and N,N-dimethylmethyleneammonium iodide (2.41 g) was added in one portion. The reaction temperature was allowed to gradually come to −40° C. over 1 hour and 20 minutes. The reaction mixture was diluted with water and extracted with methylene chloride three times. The organic layer was washed with water twice and brine, dried over anhydrous magnesium sulfate, and evaporated in vacuo. The oil obtained was purified by silica gel column chromatography (1-5% methanol-methylene chloride). The first eluted fraction contained 8,9-dihydro-10-methyl-7-methylenepyrido[1,2-a]indol-6(7H)-one (0.16 g) as an oil.

IR (Nujol): 1680, 1615, 1185 cm$^{-1}$

NMR (CDCl$_3$, δ): 2.13 (3H, s), 2.60-3.10 (4H, m), 5.60 (1H, s), 6.36 (1H, s), 7.30 (3H, s), 8.43 (1H, m)

The second eluted fraction contained 8,9-dihydro-10-methyl-7-(dimethylaminomethyl)pyrido[1,2-a]indol-6(7H)-one (1.15 g).

mp: 70°-76° C.

IR (Nujol): 1685, 1615 cm$^{-1}$

NMR (CDCl$_3$, δ): 1.70-2.10 (2H, m), 2.13 (3H, s), 2.23 (6H, s), 2.70-3.10 (5H, m), 7.30 (3H, m), 8.40 (1H, m)

PREPARATION 4

To a solution of 5-methyl-1H-imidazole-4-carbaldehyde (1.10 g) and triethylamine (1.67 ml) in acetonitrile (15 ml) at room temperature was added dimethylsulfamoyl chloride (1.18 ml). The solution was stirred at 45° C. for 20 hours. The reaction mixture was diluted with chilled water and extracted three times with methylene chloride. The organic layer was washed with water and brine, dried over anhydrous magnesium sulfate, and evaporated in vacuo. The residue was purified by silica gel column chromatography (2% methanol-methylene chloride) to give crystals (1.57 g). Recrystallization from toluene-hexane gave 4-formyl-N,N-dimethyl-5-methyl-1H-imidazole-1-sulfonamide (1.16 g).

mp: 100°-108° C.

IR (Nujol): 1690, 1560, 1190, 1165 cm$^{-1}$

NMR (DMSO-d$_6$, δ): 2.73 (3H, s), 2.98 (6H, s), 7.91 (1H, s), 10.03 (1H, s)

EXAMPLE 1

(a) To a solution of diisopropylamine (1.89 g) in tetrahydrofuran (30 ml) at −70° C. under a nitrogen atmosphere was added 1.64M n-butyllithium in hexane (11.5 ml). After being stirred at the same temperature for 20 minutes, the mixture was treated with a solution of 8,9-dihydro-10-methylpyrido[1,2-a]indol-6(7H)-one (3.39 g) in tetrahydrofuran (39 ml) over 15 minutes. The mixture was stirred at −70° C. for 30 minutes, and a solution of 5-methyl-1-trityl-1H-imidazole-4-carbaldehyde (6.0 g) in tetrahydrofuran (75 ml) was added dropwise over 20 minutes. After the mixture was stirred at −70° C. for further 55 minutes, it was diluted with water and extracted with methylene chloride. The organic layer was washed with water twice and brine, dried over anhydrous magnesium sulfate, and evaporated in vacuo to give 8,9-dihydro-7-[(hydroxy)(5-methyl-1-trityl-1H-imidazol-4-yl)methyl]-10-methylpyrido[1,2-a]indol-6(7H)-one. The product was a mixture of two diastereoisomers.

(b) The obtained oil contained two products which showed close Rf values (0.5 and 0.4 respectively) by TLC (2% methanol-chloroform). Separation with silica gel column chromatography (0.8% methanol-methylene chloride) gave two fractions. The first eluted fraction, being a mixture of two products, was crystallized from chloroform-ethyl acetate-hexane to give one isomer with an upper Rf value of 8,9-dihydro-7-[(hydroxy)(5-methyl-1-trityl-1H-imidazol-4-yl)methyl]-10-methylpyrido[1,2-a]indol-6(7H)-one (3.8 g), which was designated as the isomer A.

mp: 153°–169° C.

IR (Nujol): 1680, 1620, 1230 cm$^{-1}$

NMR (DMSO-d$_6$, δ): 1.40 (3H, s), 2.10 (3H, s), 2.00 (2H, m), 2.60–3.20 (3H, m), 5.00–5.30 (2H, m), 6.70–7.50 (19H, m), 8.27 (1H, m)

The second eluted fraction and the filtrate of the first eluted one were combined and evaporated in vacuo, giving predominantly the other isomer with a lower Rf value of 8,9-dihydro-7-[(hydroxy)(5-methyl-1-trityl-1H-imidazol-4-yl)methyl]-10-methylpyrido[1,2-a]indol-6(7H)-one (1.9 g) as an amorphous powder, which was designated as the isomer B.

NMR (DMSO-d$_6$, δ): 1.43 (3H, s), 2.10 (3H, s), 2.10 (2H, m), 2.50–3.30 (3H, m), 5.10 (1H, d, J=6 Hz), 5.33 (1H, m), 6.90–7.50 (19H, m), 8.27 (1H, m)

EXAMPLE 2

A solution of the isomer A of 8,9-dihydro-7-[(hydroxy)(5-methyl-1-trityl-1H-imidazol-4-yl)methyl]-10-methylpyrido[1,2-a]indol-6(7H)-one (0.9 g) in acetic acid-water (3.5:1, 45 ml) was stirred at 55° C. for 2.5 hours. After evaporation of the solvent, the residue was partitioned between water and methylene chloride and neutralized with an aqueous sodium bicarbonate solution to give a precipitate. Collection of the precipitate, followed by washing with water and methylene chloride, gave crystals (0.363 g), which was treated with maleic acid (0.136 g) in hot methanol (20 ml). The solution obtained was evaporated in vacuo to give an oil, which was crystallized from methanol-ether to give the isomer A of 8,9-dihydro-7-[(hydroxy)(5-methyl-1H-imidazol-4yl)-methyl]-10-methylpyrido]1,2-a]indol-6(7H)-one maleate (0.45 g).

mp: 189°–190° C.

IR (Nujol): 1685, 1635, 1615, 1575 cm$^{-1}$

NMR (DMSO-d$_6$, δ): 1.60–2.10 (2H, m), 2.10 (3H, s), 2.27 (3H, s), 2.66–3.40 (3H, m), 5.40 (1H, d, J=4.5 Hz), 6.00 (2H, s), 7.10–7.50 (3H, m), 8.20 (1H, m), 8.73 (1H, s)

EXAMPLE 3

A solution of the isomer B of 8,9-dihydro-7-[(hydroxy) (5-methyl-1-trityl-1H-imidazol-4-yl)methyl]-10-methylpyrido[1,2-a]indol-6(7H)-one (1 g) in acetic acid-water (4:1, 40 ml) was stirred at 45° C. for 4 hours and then at 60° C. for 2 hours. After evaporation of the solvent, the residue was diluted with water, neutralized with an aqueous sodium bicarbonate solution, and extracted three time with methylene chloride. The organic layer combined was washed with water and brine, dried over anhydrous magnesium sulfate, and evaporated in vacuo. Purification of the residue with silica gel column chromatography (8% methanol-methylene chloride) gave an oil (0.41 g). A solution of the oil (0.41 g) in methanol (10 ml) was treated with maleic acid (0.155 g) and evaporated. The obtained residue was crystallized from methanol-ether to give the isomer B of 8,9-dihydro-7-[(hydroxy) (5-methyl-1H-imidazol-4-yl)methyl]-10-methylpyrido[1,2-a]indol-6(7H)-one maleate (0.50 g).

mp: 155°–161° C.

IR (Nujol): 2500–3200, 1715, 1690, 1650, 1620, 1530 cm$^{-1}$

NMR (DMSO-d$_6$, δ): 2.10 (3H, s), 1.70–2.30 (3H, m), 2.23 (3H, s), 2.70–3.30 (3H, m), 5.57 (1H, d, J=3 Hz), 6.00 (2H, s), 7.10–7.50 (3H, m), 8.27 (1H, m), 8.80 (1H, s), 12.50–14.50 (2H, br s)

EXAMPLE 4

Acetic anhydride (5 ml) was added to a solution of 8,9-dihydro-7-[(hydroxy) (5-methyl-1-trityl-1H-imidazol-4-yl)methyl]-10-methylpyrido[1,2-a]indol-6(7H)-one (4 g, a mixture of the isomers A and B) in pyridine (50 ml). After being stirred at room temperature for 20 hours, the solution was evaporated in vacuo. Silica gel column chromatography (1% methanol-methylene chloride) of the oil obtained gave 7-[(acetoxy) (5-methyl-1-trityl-1H-imidazol-4-yl)methyl]-8,9-dihydro-10-methylpyrido[1,2-a]indol-6(7H)-one (4.30 g) as an amorphous powder.

IR (Nujol): 1730, 1685, 1625, 1235 cm$^{-1}$

EXAMPLE 5

To a solution of 7-[(acetoxy) (5-methyl-1-trityl-1H-imidazol-4-yl)methyl]-8,9-dihydro-10-methyl-pyrido[1,2-a]-indol-6(7H)-one (4.30 g) in toluene (60 ml) at room temperature was added 1,8-diazabicyclo[5.4.-0]undec-7-ene (5 ml). After being stirred at 55° C. for 6 hours, the solution was diluted with chilled water. The organic layer separated was washed with water three times and brine, dried over anhydrous magnesium sulfate, and evaporated in vacuo. Purification of the oil obtained with silica gel column chromatography (0.5% methanolmethylene chloride) gave 8,9-dihydro-10-methyl-7-[(5-methyl-1-trityl-1H-imidazol-4-yl)methylene]pyrido[1,2-a]-indol-6(7H)-one (3.60 g) as an amorphous powder.

IR (Nujol): 1675, 1625, 1610, 1140 cm$^{-1}$

NMR (DMSO-d$_6$, δ): 1.60 (3H, s), 2.17 (3H, s), 2.93 (2H, m), 3.60 (2H, m), 6.90–7.70 (20H, m), 8.40 (1H, m)

EXAMPLE 6

A mixture of 8,9-dihydro-10-methyl-7-[(5-methyl-1-trityl-1H-imidazol-4-yl)methylene]pyrido[1,2-a]indol-6(7H)-one (2.0 g) and 10% palladium on carbon (0.4 g) in N,N-dimethylformamide-ethanol (6:1; 49 ml) was hydrogenated at an atmospheric pressure for 6 hours. After filtration of the catalyst, the filtrate was evaporated in vacuo to give 8,9-dihydro-10-methyl-7-[(5-methyl-1-trityl-1H-imidazol-4-yl)methyl]pyrido[1,2-a]-indol-6(7H)-one as an oil, which was used in the next reaction without purification.

EXAMPLE 7

(a) A solution of crude 8,9-dihydro-10-methyl-7-[(5-methyl-1-trityl-1H-imidazol-4-yl)methyl]pyrido[1,2-a]-indol-6(7H)-one in acetic acid (50 ml) and water (15 ml) was stirred at 45° C. for 2 hours and then at 65° C. for 2 hours. After evaporation of the solvent the residue was diluted with water, neutralized with an aqueous sodium bicarbonate solution, and extracted three times with methylene chloride. The organic layer combined was washed with water and brine, dried over anhydrous magnesium sulfate, and evaporated in vacuo. Purification of the residue with silica gel column chromatography (10% methanol-methylene chloride) gave 8,9-dihydro-10-methyl-7-[(5-methyl-1H-imidazol-4-yl)methyl]pyrido[1,2-a]indol-6(7H)-one (1.0 g) as crystals.

mp: 226°–229° C.

IR (Nujol): 1690, 1615, 1325 cm$^{-1}$

NMR (DMSO)-d$_6$, δ): 1.60–2.10 (2H, m), 2.10 (6H, s), 2.50–3.40 (5H, m), 7.17–7.60 (3H, m), 7.37 (1H, s), 8.33 (1H, m), 11.60 (1H, s)

(b) The above obtained crystals were treated with maleic acid (0.396 g) in methanol (30 ml). After evaporation of the solvent, the residue obtained was crystallized from methanol-ether to give 8,9-dihydro-10-methyl-7-[(5-methyl-1H-imidazol-4-yl)methyl]pyrido[1,2-a]indol-6(7H)-one maleate (1.06 g).

mp: 176°–178° C.

IR (Nujol): 2200–2600, 1690, 1640, 1620, 1555 cm$^{-1}$

NMR (DMSO-d$_6$, δ): 1.66–2.20 (2H, m), 2.13 (3H, s), 2.23 (3H, s), 2.60–3.40 (5H, m), 6.00 (2H, s), 7.10–7.60 (3H, m), 8.27 (1H, m), 8.77 (1H, s), 11.00–14.00 (2H, m)

EXAMPLE 8

A solution of 8,9-dihydro-10-methyl-7-[(5-methyl-1-trityl-1H-imidazol-4-yl)methylene]pyrido[1,2-a]indol-6(7)-one (0.9 g) in acetic acid-water (4:1, 50 ml) was stirred at 60° C. for 2.5 hours.

After evaporation of the solvent, the residue was diluted with an aqueous sodium bicarbonate solution and extracted with methylene chloride. The organic layer was washed with water and brine, dried over anhydrous magnesium sulfate, and evaporated in vacuo. Purification of the residue with silica gel column chromatography (2% methanol-chloroform), followed by recrystallization from methanol-chloroform-hexane, gave 8,9-dihydro-10-methyl-7-[(5-methyl-1H-imidazol-4-yl)methylene]pyrido[1,2-a]indol-6(7H)-one (0.41 g).

mp: 252°–255° C.

IR (Nujol): 1665, 1625, 1595, 1555, 1140 cm$^{-1}$

NMR (DMSO-d$_6$, δ): 2.16 (3H, s), 2.33 (3H, s), 2.96 (2H, t, J=6 Hz), 3.53 (2H, t, J=6 Hz), 7.10–7.60 (3H, m), 7.63 (1H, s), 7.70 (1H, s), 8.40 (1H, m)

EXAMPLE 9

(a) 8,9-Dihydro-7-[(hydroxy) (5-methyl-1-trityl-1H-imidazol-4-yl)methyl]-10-propylpyrido[1,2-a]indol-6(7H)-one was prepared in a similar manner to that of Example 1-(a).

IR (Nujol): 1705, 1610, 1230 cm$^{-1}$

The product was a mixture of two diastereoisomers and used in the next reaction without separation.

(b) a solution of 8,9-dihydro-7-[(hydroxy) (5-methyl-1-trityl-1H-imidazol-4-yl)methyl]-10-propylpyrido[1,2-a]-indol-6(7H)-one (1.65 g) in a mixture of acetic acid and water (4:1, 90 ml) was stirred at 60° C. for 4 hours. After evaporation of the solvent, the residue was diluted with as aqueous sodium bicarbonate solution and extracted three times with methylene chloride. The organic layer was washed with water and brine, dried over anhydrous magnesium sulfate, and evaporated in vacuo. The crystalline residue was suspended in a mixture of methanol and chloroform and filtered to give one isomer of 8,9-dihydro-7-[(hydroxy) (5-methyl-1H-imidazol-4-yl)methyl]-10-propylpyrido[1,2-a]indol-6(7H)-one with an upper Rf value in silica gel thin layer chromatography (TLC) (6% methanol-chloroform) (0.27 g), which was designated as the isomer A. The filtrate was evaporated and purified by silica gel column chromatography (6% methanol-methylene chloride). The fractions eluted first contained the isomer A and the fractions eluted later contained another isomer of 8,9-dihydro-7-[(hydroxy) (5methyl-1H-imidazol-4-yl)methyl]-10-propylpyrido[1,2-a]indol-6(7H)-one with a lower Rf value in TLC, which was designated as the isomer B.

The isomer A combined was recrystallized from methanol to give 326 mg of the product.

mp: 190°–192° C.

IR (Nujol): 3430, 1690, 1660, 1620 cm$^{-1}$

NMR (DMSO-d$_6$, δ): 0.89 (3H, t, J=9 Hz), 1.57 (2H, m), 2.17 (5H, br s), 2.54 (2H, t, J=7 Hz), 2.60–3.00 (2H, m), 3.20 (1H, m), 4.80–5.80 (2H, m), 7.23 (2H, m), 7.36 (1H, s), 7.50 (1H, m), 8.30 (1H, m), 11.68 (1H, s)

The isomer B was recrystallized from methanol-chloroform-hexane to give 302 mg of the product.

mp: 220°–223° C.

IR (Nujol): 3230, 1660, 1615, 1590 cm$^{-1}$

NMR (DMSO-d$_6$, δ): 0.90 (3H, t, J=7.2 Hz), 1.58 (2H, m), 2.04 (2H, m), 2.19 (3H, s), 2.60 (2H, t, J=7.2 Hz), 2.60–3.20 (2H, m), 3.33 (1H, m), 5.25 (1H, br s), 5.57 (1H, br s), 7.25 (2H, m), 7.42 (1H, s), 7.50 (1H, m), 8.36 (1H, m), 11.70 (1H, s)

EXAMPLE 10

7[Acetoxy) (5-methyl-1-trityl-1H-imidazol-4-yl)-methyl]-8,9-dihydro-10-propylpyrido[1,2-a]indol-6(7H)-one was prepared in a similar manner to that of Example 4 as an amorphous powder.

IR (Nujol): 1725, 1695, 1610 cm$^{-1}$

EXAMPLE 11

8,9-Dihydro-7-[(5-methyl-1-trityl-1H-imidazol-4-yl)methylene]-10-propylpyrido[1,2-a]indol-6(7H)-one was prepared in a similar manner to that of Example 5 as an amorphous powder.

IR (Nujol): 1675, 1615 cm$^{-1}$

EXAMPLE 12

8,9-Dihydro-7-[(5-methyl-1-trityl-1H-imidazol-4-yl)methyl]-10-propylpyrido[1,2-a]indol-6(7H)-one was prepared in a similar manner to that of Example 6.

EXAMPLE 13

The suspension of 8,9-dihydro-10-methyl-7-[(5-methyl-1H-imidazol-4-yl)methyl]pyrido[1,2-a]indol-6(7H)-one (2.0 g) in methanol (60 ml) was treated with hydrogen chloride in ethanol and then diluted with hot aqueous ethanol (water:ethanol, 1:4) to give a clear solution. After filtration of the insoluble materials, the filtrate was evaporated under reduced pressure to about 40 ml and allowed to stand at room temperature overnight. Filtration, followed by washing with ethanol, gave 8,9-dihydro-10-methyl-7-[(5-methyl-1H-imidazol-4-yl)methyl[pyrido[1,2-a]indol-6(7H)-one hydrochloride (2.10 g) as crystals.

mp: >250° C.

IR (Nujol): 1695, 1635, 1520 cm$^{-1}$

NMR (DMSO-d$_6$, δ): 1.66–2.10 (2H, m), 2.13 (3H, s), 2.23 (3H, s), 2.60–3.40 (5H, m), 7.27 (2H, m), 7.43 (1H, m), 8.23 (1H, m), 8.90 (1H, s)

EXAMPLE 14

8,9-Dihydro-7-[(5-methyl-1H-imidazol-4-yl)methyl]-10-propylpyrido[1,2-a]indol-6(7H)-one hydrochloride was prepared in a similar manner to that of Example 7-(a), and then Example 13.

mp: 193°-199° C.

IR (Nujol): 3350, 1690, 1660, 1640, 1615 cm$^{-1}$

NMR (DMSO-d$_6$, δ): 0.90 (3H, t, J=7.3 Hz), 1.68 (2H, m), 1.70-2.20 (2H, m), 2.27 (3H, s), 2.60 (2H, t, J=7.3 Hz), 2.65-3.50 (5H, m), 7.26 (2H, m), 7.52 (1H, m), 8.33 (1H, m), 8.96 (1H, s), 14.45 (2H, br s)

EXAMPLE 15

8,9-Dihydro-7-[(hydroxy) (1-trityl-1H-imidazol-4-yl)methyl]-10-methylpyrido[1,2-a]indol-6(7H)-one (a mixture of the isomers A and B) was prepared in a similar manner to that of Example 1-(a).

IR (Nujol): 1710, 1685, 1660 cm$^{-1}$

NMR (CDCl$_3$, δ): 5.53 (1H, m), 3.51 (1H, d, J=7 Hz), 5.20 (1H, m), 4.66 (1H, d, J=4 Hz)

EXAMPLE 16

7-[(Acetoxy) (1-trityl-1H-imidazol-4-yl)methyl]-8,9-dihydro-10-methylpyrido[1,2-a]indol-6(7H)-one was prepared in a similar manner to that of Example 4.

IR (Nujol): 1735, 1680 cm$^{-1}$

NMR (CDCl$_3$, δ): 1.95 (3H, s), 2.14 (3H, s)

EXAMPLE 17

8,9-Dihydro-10-methyl-7-[(1-trityl-1H-imidazol-4-yl)methylene]pyrido[1,2-a]indol-6(7H)-one was prepared in a similar manner to that of Example 5.

mp: 179°-181° C.

IR (Nujol): 1670, 1620, 1610 cm$^{-1}$

NMR (DMSO-d$_6$, δ): 8.35 (1H, dd, J=6 Hz, J=3 Hz), 7.7-6.9 (21H, m), 3.44 (2H, br t, J=6 Hz), 2.97 (2H, br t, J=6 Hz), 2.16 (3H, s)

EXAMPLE 18

8,9-Dihydro-10-methyl-7-[(1-trityl-1H-imidazol-4-yl)methyl]pyrido[1,2-a]indol-6(7H)-one was prepared in a similar manner to that of Example 6, which was used in the next reaction without purification.

EXAMPLE 19

To a mixture of acetic acid (50 ml) and water (15 ml), was added 8,9-dihydro-10-methyl-7-[(1-trityl-1H-imidazol-4-yl)methyl]pyrido[1,2-a]indol-6(7H)-one (4.93 g), and stirred at 60° C. for 2 hours. After being cooled, the precipitates were filtered off. The filtrate was neutralized with aqueous 8N-sodium hydroxide solution, and extracted with chloroform. The organic layer was washed with brine, dried over sodium sulfate, and evaporated. The residue was crystallized from diisopropyl ether-ethyl acetate (5:1, V/V) to give 8,9-dihydro-7-[(1H-imidazol-4-yl)methyl]-10-methylpyrido[1,2-a]indol-6(7H)-one (1.84 g).

mp: 156°-157° C.

IR (Nujol): 1685 cm$^{-1}$

NMR (DMSO-d$_6$, δ): 8.34 (1H, dt, J=6Hz, J=3 Hz, J=3 Hz), 7.76 (1H, s), 7.46 (1H, dd, J=6 Hz, J=3 Hz), 7.4-7.2 (2H, m), 6.94 (1H, s), 3.25 (1H, dd, J=7 Hz, J=2 Hz), 3.2-3.0 (2H, m), 2.9-2.7 (2H, m), 2.13 (3H, s), 2.2-2.0 (1H, m), 1.8-1.6 (1H, m)

MS (m/e): 279 (M$^+$)

EXAMPLE 20

(+)-Di-p-toluoyl-D-tartaic acid (4.68 g) and 8,9-dihydro-10-methyl-7-[(5-methyl-1H-imidazol-4-yl)methyl]-pyrido[1,2-a]indol-6(7H)-one (3.55 g) were dissolved in hot methanol (200 ml). After removal of the solvent (100 ml), the solution was diluted with ethanol (200 ml) and allowed to stand at 5° C. for 3 days. The precipitates formed was collected and washed with methanol. Recrystallization of the precipitates from methanol (200 ml) at 5° C. gave crystals, which were neutralized with an aqueous sodium bicarbonate solution and extracted with chloroform. The chloroform layer was washed with water, dried over anhydrous magnesium sulfate, and evaporated in vacuo. The crystals obtained were purified by silica gel column chromatography (10% methanol-chloroform) and then recrystallized from methanol-chloroform-hexane. After filtration of the crystals, the filtrate was evaporated in vacuo to give (−)-8,9-dihydro-10-methyl-7-[(5-methyl-1H-imidazol-4-yl)methyl]pyrido[1,2-a]indol-6(7H)-one (0.4 g) with $[\alpha]_D^{25} = -56°$ (C=1.0, 10% methanol-chloroform) as crystals. A part of the crystals (200 mg) were treated with hydrochloric acid in methanol and recrystallized from methanol-ether to give (−)-8,9-dihydro-10-methyl-7-[(5-methyl-1H-imidazol-4-yl)methyl]pyrido[1,2-a]indol-6(7H)-one hydrochloride (0.2 g).

mp: >250° C.

EXAMPLE 21

(+)-8,9-Dihydro-10-methyl-7-[(5-methyl-1H-imidazol-4-yl)methyl]pyrido[1,2-a]indol-6(7H)-one hydrochloride was prepared in a similar manner to that of Example 20 except that (−)-di-p-toluoyl-L-tartaric acid was used in place of (+)-di-p-toluoyl-D-tartaric acid.

Hydrochloride: mp. >250° C.

The free base: $[\alpha]_D^{25} = +60°$ (C=1, 10% methanol-chloroform)

EXAMPLE 22

To a solution of diisopropylamine (658 mg) in tetrahydrofuran (8 ml) at −70° C. under nitrogen atmosphere was added 1.64M butyllithium in hexane (3.96 ml). After being stirred at the same temperature for 20 minutes, the mixture was treated with a solution of 8,9-dihydropyrido[1,2-a]indol-6(7H)-one (1.21 g) in tetrahydrofuran (12 ml) over 15 minutes. The mixture was stirred at −70° C. for 30 minutes, and a solution of 5-methyl-1-trityl-1H-imidazole-4-carbaldehyde (2.29 g) in tetrahydrofuran (20 ml) was added dropwise over 20 minutes. After the mixture was stirred at −70° C. for further 60 minutes and at ambient temperature for 2 hours, it was diluted with water and neutralized with an aqueous solution of oxalic acid. Separated organic layer was washed with brine, dried over anhydrous magnesium sulfate, and evaporated in vacuo to give 8,9-dihydro-7-[(hydroxy) (5-methyl-1-trityl-1H-imidazol-4-yl)methyl]pyrido[1,2-a]indol-6(7H)-one (2.21 g) as an amorphous powder. The product was a mixture of two diastereoisomers.

mp: 85°-90° C.

IR (Nujol): 1690, 1590 cm$^{-1}$

NMR (CDCl$_3$, δ): 1.46 (3H, s), 1.6-2.4 (2H, m), 2.8-3.5 (3H, m), 4.8-5.2 (1H, m), 6.29 (1H, s), 7.0-7.4 (18H, m), 8.3-8.5 (1H, m)

EXAMPLE 23

A solution of 8,9-dihydro-7-[(hydroxy) (5-methyl-1-trityl-1H-imidazol-4-yl)methyl]pyrido[1,2-a]indol-6(7H)-one (1.1 g) in acetic acid-water (3:1, 48 ml) was stirred at 65° C. for 90 minutes. After evaporation of the solvent, the residue was diluted with water, neutralized with an aqueous solution of sodium hydrogencarbonate, and extracted with chloroform. The organic layer was washed with brine, dried over anhydrous magnesium sulfate, and evaporated in vacuo. The obtained amorphous powder contained two products which showed close Rf values (0.3 and 0.4 respectively) by TLC (20% methanol-chloroform). Separation with silica gel column chromatography (10% methanol-chloroform) gave two fractions. The residue obtained from the first eluted fraction was dissolved in ethyl acetate and treated with hydrogen chloride in ether to give one isomer with an upper Rf value of 8,9-dihydro-7-[(hydroxy) (5-methyl-1H-imidazol-4-yl)methyl]pyrido[1,2-a]indol-6(7H)-one hydrochloride (86.1 mg), which was designated as the isomer A.

mp: 180°–183° C. (dec.)

IR (Nujol): 3300, 1680, 1595 cm$^{-1}$

NMR (DMSO-d$_6$, δ): 1.5–2.0 (1H, m), 2.32 (3H, s), 2.8–3.6 (5H, m), 5.48 (1H, br s), 6.43 (1H, s), 7.1–7.6 (3H, m), 8.2–8.3 (1H, m), 8.94 (1H, s), 14.3 (1H, s)

MS (m/e): 295 (M$^+$)

The second eluted fraction was evaporated in vacuo, followed by recrystallization from ethyl acetate to give the other isomer with a lower Rf value of 8,9-dihydro-7-[(hydroxy) (5-methyl-1H-imidazol-4-yl)methyl]pyrido[1,2-a]indol-6(7H)-one (45 mg), which was designated as the isomer B.

mp: 186°–188° C. (dec.)

IR (Nujol): 3400, 1655, 1590 cm$^{-1}$

NMR (DMSO-d$_6$, δ): 1.8–2.2 (2H, m), 2.20 (3H, s), 2.7–3.3 (3H, m), 5.30 (1H, br s), 5.58 (1H, s), 6.41 (1H, s), 7.2–7.6 (3H, m), 7.43 (1H, s), 8.3–8.4 (1H, m)

MS (m/e): 295 (M$^+$)

EXAMPLE 24

Acetic anhydride (1.26 g) was added to a solution of 8,9-dihydro-7-[(hydroxy) (5-methyl-1-trityl-1H-imidazol-4-yl)methyl]pyrido[1,2-a]indol-6(7H)-one (1.34 g, a mixture of the isomers A and B) in pyridine (20 ml). After being stirred at 60° C. for 2 hours, the solution was evaporated in vacuo. The residue obtained was diluted with chloroform and neutralized with an aqueous sodium hydrogencarbonate solution. The separated organic layer was dried over anhydrous magnesium sulfate and evaporated in vacuo to give 7-[(acetoxy) (5-methyl-1-trityl-1H-imidazol-4-yl)methyl]-8,9-dihydropyrido[1,2-a]indol-6(7H)-one as an oil, which was used in the next reaction without purification.

EXAMPLE 25

To a solution of 7-[(acetoxy)(5-methyl-1-trityl-1H-imidazol-4-yl)methyl]-8,9-dihydropyrido[1,2-a]indol-6(7H)-one in toluene (30 ml) at room temperature was added 1,8-diazabicyclo[5.4.0]undec-7-ene (762 mg). After being stirred at 55° C. for 2 hours, the solution was evaporated in vacuo. The residue was diluted with chloroform, washed with water, and dried over anhydrous magnesium sulfate. After evaporation of the solvent, the residue obtained was purified with silica gel column chromatography (eluent:chloroform) to give 8,9-dihydro-7-[(5-methyl-1-trityl-1H-imidazol-4-yl)methylene]pyrido[1,2-a]indol-6(7H)-one (1.3 g).

mp: 214°–217° C.

IR (Nujol): 1675, 1620, 1570 cm$^{-1}$

NMR (DMSO-d$_6$, δ): 1.61 (3H, s), 3.03 (2H, t, J=6.87 Hz), 3.60 (2H, t, J=6.87 Hz), 6.47 (1H, s), 7.0–7.7 (20H, m), 8.3–8.5 (1H, m)

EXAMPLE 26

8,9-Dihydro-7-[(5-methyl-1H-imidazol-4-yl)methyl]pyrido[1,2-a]indol-6(7H)-one hydrochloride was prepared from 8,9-dihydro-7-[(5-methyl-1-trityl-1H-imidazol-4-yl)methylene]pyrido[1,2-a]indol-6(7H)-one in a similar manner to that of Example 36.

mp: 262°–264° C. (dec.)

IR (Nujol): 1695, 1640, 1595 cm$^{-1}$

NMR (DMSO-d$_6$, δ): 1.7–2.1 (2H, m), 2.27 (3H, s), 2.8–3.4 (5H, m), 6.45 (1H, s), 7.2–7.6 (3H, m), 8.2–8.4 (1H, m), 8.98 (1H, s)

MS (m/e): 279 (M$^+$)

EXAMPLE 27

To a solution of diisopropylamine (557 mg) in tetrahydrofuran (15 ml) at −70° C. under a nitrogen atmosphere was added 1.64M butyllithium in hexane (3.35 ml). After being stirred at the same temperature for 20 minutes, the mixture was treated with a solution of 8,9-dihydro-10-methylpyrido[1,2-a]indol-6(7H)-one (995 mg) in tetrahydrofuran (10 ml) over 15 minutes. The mixture was stirred at −70° C. for 30 minutes, and a solution of 1-trityl-1H-imidazole-2-carbaldehyde (1.69 g) in tetrahydrofuran (20 ml) was added dropwise over 10 minutes. After the mixture was stirred at −70° C. for further 70 minutes, it was diluted with chilled water, neutralized with an aqueous solution of oxalic acid, and extracted with chloroform. The organic layer was washed with brine, dried over anhydrous magnesium sulfate, and evaporated in vacuo. Purification of the residue with silica gel column chromatography (20% ethyl acetate-chloroform) gave 8,9-dihydro-7-[(hydroxy)-(1-trityl-1H-imidazol-2-yl)methyl]-10-methylpyrido[1,2-a]indol-6(7H)-one (1.85 g)

mp: 209°–210° C. (dec.)

IR (Nujol): 3300, 1660, 1615 cm$^{-1}$

NMR (CDCl$_3$, δ): 1.1–1.2(1H, m), 1.9–2.2 (1H, m), 2.08 (3H, s), 2.4–2.7 (2H, m), 3.2–3.4 (1H, m), 4.5–4.7 (2H, m), 6.9–7.3 (20H, m), 8.2–8.4 (1H, m)

MS (m/e): 519 (M$^+$)

EXAMPLE 28

A solution of 8,9-dihydro-7-[(hydroxy)(1-trityl-1H-imidazol-2-yl)methyl]-10-methylpyrido]1,2-a]indol-6(7H)-one (376 mg) in acetic acid (15 ml) and water (5 ml) was stirred at 60° C. for 2.5 hours. After evaporation of the solvent, the residue was diluted with water, neutralized with an aqueous solution of sodium hydrogencarbonate, and extracted three times with chloroform. The organic layer was washed with brine, dried over anhydrous magnesium sulfate, and evaporated in vacuo. Purification of the residue with silica gel column chromatography (15% methanol-chloroform), followed by recrystallization from methanol, gave 8,9-dihydro-7-[(hydroxy)(1H-imidazol-2-yl)methyl]-10-methylpyrido[1,2-a]indol-6(7H)-one (148 mg).

mp: 199°–200° C.

IR (Nujol): 3400, 1668, 1620 cm$^{-1}$

NMR (CDCl$_3$, δ): 1.8–2.1 (2H, m), 2.15 (3H, s), 2.7–2.9 (1H, s), 3.0–3.2 (2H, m), 3.61 (2H, br s), 5.24 (1H, d, J=6.07 Hz), 6.99 (1H, s), 7.00 (1H, s), 7.2–7.5 (3H, m), 8.3–8.5 (1H, m)

MS (m/e): 295 (M$^+$)

EXAMPLE 29

7-[(Acetoxy)(1-trityl-1H-imidazol-2-yl)methyl]-8,9-dihydro-10-methylpyrido[1,2-a]indol-6(7H)-one was prepared in a similar manner to that of Example 4, which was used in the next reaction without purification.

EXAMPLE 30

8,9-Dihydro-10-methyl-7-[(1-trityl-1H-imidazol-2-yl)methylene]pyrido[1,2-a]indol-6(7H)-one was prepared in a similar manner to that of Example 5.

mp: 222°–224° C. (dec.)
IR (Nujol): 1670, 1620, 1600 cm$^{-1}$
NMR (DMSO-d$_6$, δ): 2.13 (3H, s), 2.7–3.1 (2H, m), 3.2–3.4 (2H, m), 6.8–7.5 (21H, m), 8.11 (1H, dd, J=2.93 Hz, 6.81 Hz)

EXAMPLE 31

A mixture of 8,9-dihydro-10-methyl-7-[(1-trityl-1H-imidazol-2-yl)methylene]pyrido[1,2-a]indol-6(7H)-one (950 mg), ammonium formate (573 mg) and 10% palladium on carbon (285 mg) in acetic acid (19 ml) was stirred at 110° C. for 1 hour. After filtration of the catalyst, the filtrate was evaporated in vacuo. The residue was diluted with chloroform. The chloroform solution was washed with 1N hydrochloric acid (5 ml×2) to give a precipitate which was collected, washed with water, and dried to give 8,9-dihydro-10-methyl-7-[(1H-imidazol-2-yl)methyl]pyrido[1,2-a]indol-6(7H)-one hydrochloride (445.6 mg).

mp: >270° C.
IR (Nujol): 2660, 1665, 1630 cm$^{-1}$
NMR (DMSO-d$_6$, δ): 1.8–2.1 (2H, m), 2.15 (3H, s), 2.8–3.8 (6H), 7.2–7.3 (2H, m), 7.4–7.5 (1H, m), 7.61 (2H, s), 8.2–8.3 (1H, m), 14.6 (1H, br s)
MS (m/e): 279 (M+)

EXAMPLE 32

7-[(1-Benzyl-1H-2,5-dimethylimidazol-4-yl)(hydroxy)methyl]-8,9-dihydro-10-methylpyrido[1,2-a]indol-6(7H)-one was prepared in a similar manner to that of Example 27.

mp: 121°–124° C.
IR (Nujol): 3400, 1670, 1620 cm$^{-1}$
NMR (CDCl$_3$, δ): 1.4–1.6 (2H, m), 1.7–2.0 (2H, m), 2.06 (3H, s), 2.19 (3H, s), 2.36 (3H, s), 2.7–2.9 (1H, m), 5.0–5.9 (3H, m), 6.9–7.1 (2H, m), 7.2–7.5 (6H, m), 8.3–8.5 (1H, m)

EXAMPLE 33

A mixture of 7-[(1-benzyl-1H-2,5-dimethylimidazol-4-yl)(hydroxy)methyl]-8,9-dihydro-10-methylpyrido[1,2-a]indol-6(7H)-one (1.70 g), ammoniumformate (7.78 g) and 10% palladium on carbon (0.5 g) in acetic acid (30 ml) was stirred at 120° C. for 4 hours. After filtration of the catalyst, the filtrate was evaporated in vacuo. The residue was diluted with chloroform, washed with 10% aqueous solution of sodium hydrogencarbonate, and dried over anhydrous magnesium sulfate. After the solvent was evaporated in vacuo, the residue was subjected to column chromatography on silica gel (10% methanol-chloroform). Fractions containing the product were combined and evaporated in vacuo. The residue was crystallized from ethyl acetate to give 8,9-dihydro-10-methyl-7-[(2,5-dimethyl-1H-imidazol-4-yl)methyl]pyrido[1,2-a]indol-6(7H)-one (0.36 g).

mp: 219°–221° C.
IR (Nujol): 1690, 1620, 1545 cm$^{-1}$
NMR (DMSO-d$_6$, δ): 1.6–1.85 (1H, m), 1.9–2.1 (1H, m), 2.05 (3H, s), 2.13 (3H, s), 2.19 (3H, s), 2.5–2.8 (2H, m), 2.9–3.2 (3H, m), 7.2–7.3 (2H, m), 7.4–7.5 (1H, m), 8.3–8.4 (1H, m)
MS (m/e): 307 (M$^{30}$)

EXAMPLE 34

(a) To a solution of diisopropylamine (1.01 g) in tetrahydrofuran (15 ml) at −70° C. under a nitrogen atmosphere was added 1.64M butyllithium in hexane (6.1 ml). After being stirred at the same temperature for 20 minutes, the mixture was treated with a solution of 8,9-dihydro-10-methylpyrido[1,2-a]indol-6(7H)-one (1.99 g) in tetrahydrofuran (25 ml) over 20 minutes. The mixture was stirred at −70° C. for 30 minutes, and a solution of 2-methyl-3-pyridinecarbaldehyde (1.21 g) in tetrahydrofuran (20 ml) was added dropwise over 20 minutes. After the mixture was stirred at −70° C. for further 60 minutes and at ambient temperature for 60 minutes, it was diluted with water and adjusted to pH 9 with oxalic acid. The separated organic layer was washed with brine, dried over anhydrous magnesium sulfate, and evaporated in vacuo, to give 8,9-dihydro-7-[(hydroxy)(2-methylpyridin-3-yl)methyl]-10-methylpyrido[1,2-a]indol-6(7H)-one.

The product was a mixture of two diastereoisomers.

(b) The obtained oil contained two products which showed close Rf values (0.3 and 0.4 respectively) by TLC (20% ethyl acetate-chloroform). Separation with silica gel column chromatography (20% ethyl acetate-chloroform) gave two fractions. The solid obtained from the first eluted fraction was treated with hydrogen chloride in a mixture of ethyl acetate-chloroform-ether to give one isomer with an upper Rf value of 8,9-dihydro-7-[(hydroxy)(2-methylpyridin-3-yl)methyl]-10-methylpyrido[1,2-a]indol-6(7H)-one hydrochloride (0.45 g), which was designated as the isomer A.

mp: 232°–233° C. (dec.)
IR (Nujol): 3260, 2500, 1690, 1610 cm$^{-1}$
NMR (DMSO-d$_6$, δ): 2.15 (3H, s), 2.23 (2H, t, J=5.51 Hz), 2.85 (3H, s), 2.7–3.0 (1H, m), 3.1–3.4 (2H, m), 5.30 (1H, d, J=2.18 Hz), 7.1–7.5 (3H, m), 7.94 (1H, dd, J=5.76 Hz, 6.99 Hz), 8.1–8.3 (1H, m), 8.6–8.8 (2H, m)
MS (m/e): 320 (M+)

The second eluted fraction was evaporated in vacuo, and treated in a similar manner to that of an upper Rf value to give the other isomer with a lower Rf value of 8,9-dihydro-7-[(hydroxy)(2-methylpyridin-3-yl)methyl]-10-methylpyrido[1,2-a]indol-6(7H)-one hydrochloride (74.3 mg), which was designated as the isomer B.

mp: 213°–214° C. (dec.)
IR (Nujol): 3200, 2500, 1690, 1615 cm$^{-1}$
NMR (DMSO-d$_6$, δ): 1.6–1.8 (2H, m), 1.9–2.0 (1H, m), 2.15 (3H, s), 2.6–2.9 (1H, m), 2.80 (3H, s), 3.0–3.3 (2H, m), 5.83 (1H, s), 7.2–7.4 (3H, m), 7.95 (1H, dd, J=5.44 Hz, 7.42 Hz), 8.3–8.4 (1H, m), 8.57 (1H, d, J=7.42 Hz), 8.71 (1H, d, J=5.45 Hz)
MS (m/e): 320 (M+)

EXAMPLE 35

Acetic anhydride (2.24 g) was added to a solution of 8,9-dihydro-7-[(hydroxy)(2-methylpridin-3-yl)methyl]-10-methylpyrido[1,2-a]indol-6(7H)-one (1.35 g, a mixture of the isomers A and B) in pyridine (20 ml). After being stirred at 60° C. for 2 hours, the solution was evaporated in vacuo. The residue was diluted with chloroform, washed with brine, dried over anhydrous magnesium sulfate, and evaporated in vacuo. The residue and 1,8-diazabicyclo[5.4.0]undec-7-ene (1.27 g) were dissolved in toluene (30 ml). The solution was stirred at 60° C. for 2 hours and evaporated in vacuo. The residue was crystallized from ethyl acetate to give 8,9-dihydro-10-methyl-7-[(2-methylpyridin-3-yl)methylene]pyrido[1,2-a]indole-6(7H)-one (0.92 g).

mp: 182°–183° C.

IR (Nujol): 1675, 1630, 1610 cm$^{-1}$

NMR (DMSO-d$_6$, δ): 2.17 (3H, s), 2.51 (3H, s), 2.6–3.0 (4H, m), 7.2–7.4 (3H, m), 7.4–7.6 (1H, m), 7.70 (1H, d, J=7.4 Hz), 7.88 (1H, s), 8.3–8.6 (2H, m)

MS (m/e): 302 (M$^+$)

EXAMPLE 36

A mixture 8,9-dihydro-10-methyl-7-[(2-methylpyridin-3-yl)methylene]pyrido[1,2-a]indole-6(7H)-one (820 mg), ammonium formate (854 mg) and 10% palladium on carbon (0.3 g) in acetic acid (30 ml) was stirred at 110° C. for 1 hour. After filtration of the catalyst, the filtrate was evaporated in vacuo. The residue was diluted with 5% methanol in chloroform, washed with 5% aqueous solution of sodium hydrogencarbonate and brine, dried over anhydrous magnesium sulfate, and evaporated in vacuo. Purification of the residue with silica gel column chromatography (5% methanol-chloroform) gave 0.7 g of crystals, which were dissolved in a mixture of chloroform and ethyl acetate and treated with hydrogen chloride in ether to give 8,9-dihydro-10-methyl-7-[(2-methylpyridin-3-yl)methyl]-pyrido[1,2-a]indol-6(7H)-one hydrochloride (0.43 g).

mp: 237°–239° C. (dec.)

IR (Nujol): 1690, 1615, 1545 cm$^{-1}$

NMR (DMSO-d$_6$, δ): 1.8–2.1 (2H, m), 2.15 (3H, s), 2.82 (3H, s), 2.9–3.7 (5H, m), 7.2–7.3 (2H, m), 7.4–7.6 (1H, m), 7.87 (1H, dd, J=5.80, 6.67 Hz), 8.2–8.4 (1H, m), 8.46 (1H, d, J=6.67 Hz), 8.68 (1H, dd, J=1.33, 6.67 Hz)

MS (m/e): 304 (M$^+$)

EXAMPLE 37

8,9-Dihydro-7-[(hydroxy)(pyridin-3-yl)methyl]-10-methylpyrido[1,2-a]indol-6(7H)-one was prepared in a similar manner to that of Example 27.

mp: 83°–86° C.

IR (Nujol): 1685, 1615 cm$^{-1}$

NMR (DMSO-d$_6$, δ): 1.6–2.1 (2H, m), 2.14 (3H, d, J=1.24 Hz), 2.5–3.1 (3H, m), 3.76 (1/2H, br s), 5.10 (1/2H, d, J=8.7 Hz), 5.44 (1/2H, s), 5.80 (1/2H, s), 7.2–7.4 (4H, m), 7.7–7.9 (1H, m), 8.4–8.7 (3H, m)

EXAMPLE 38

8,9-Dihydro-10-methyl-7-[(pyridin-3-yl)methylene]-pyrido[1,2-a]indol-6(7H)-one was prepared in a similar manner to that of Example 35.

mp: 102°–103° C.

IR (Nujol): 1670, 1630, 1615 cm$^{-1}$

NMR (DMSO-d$_6$, δ): 2.20 (3H, s), 2.9–3.1 (4H, m), 7.2–7.5 (4H, m), 7.7–7.8 (1H, m), 7.96 (1H, s), 8.4–8.6 (1H, m), 8.60 (1H, dd, J=1.60, 4.83 Hz), 8.69 (1H, d, J=2.2 Hz)

MS (m/e): 288 (M$^+$)

EXAMPLE 39

A solution of 8,9-dihydro-10-methyl-7-[(pyridin-3-yl)methylene]pyrido[1,2-a]indol-6(7H)-one (520 mg), ammonium formate (568 mg) and 10% palladium on carbon (200 mg) in acetic acid (20 ml) was stirred at 110° C. for 2 hours. After filtration of the catalyst, the filtrate was evaporated in vacuo. The residue was diluted with 10% methanol-chloroform. The solution was washed with 5% aqueous solution of sodium hydrogencarbonate and brine, dried over anhydrous magnesium sulfate, and evaporated in vacuo. Purification of the residue with silica gel chromatography (5% methanol-chloroform), followed by recrystallization from ethyl acetate-ether, gave 8,9-dihydro-10-methyl-7-[(pyridin-3-yl)methyl]pyrido[1,2-a]indol-6(7H)-one (273 mg).

mp: 158°–160° C.

IR (Nujol): 1690, 1675, 1620 cm$^{-1}$

NMR (CDCl$_3$, δ): 0.9–2.0 (2H, m), 2.13 (3H, s), 2.4–3.6 (5H, m), 7.0–7.7 (5H, m), 8.3–8.6 (3H, m)

MS (m/e): 290 (M$^+$)

EXAMPLE 40

To a solution of diisopropylamine (557 mg) in tetrahydrofuran (7.5 ml) at −70° C. under a nitrogen atmosphere was added 1.64M butyllithium in hexane (3.35 ml). After being stirred at the same temperature for 20 minutes, the mixture was treated with a solution of 8,9-dihydro-10-methylpyrido[1,2-a]indol-6(7H)-one (995 mg) in tetrahydrofuran (10 ml) over 15 minutes. The mixture was stirred at −70° C. for 40 minutes, and a solution of 2-methyl-1-trityl-1H-imidazole-4-carbaldehyde (1.76 g) in tetrahydrofuran (20 ml) was added dropwise over 15 minutes. After the mixture was stirred at −70° C. for 1 hour and at ambient temperature for 1 hour, it was diluted with water and neutralized with a aqueous solution of oxalic acid. The organic layer was separated and the aqueous layer was extracted with chloroform. The organic layers were combined and washed with brine and dried over anhydrous magnesium sulfate. After the solvent was evaporated in vacuo, the residue was subjected to a column chromatography on silica gel (20% ethyl acetate-chloroform). The fractions containing the product were combined and evaporated in vacuo. The residue was crystallized from n-hexane-ether to give 8,9-dihydro-7[(hydroxy)(2-methyl-1-trityl-1H-imidazol-4-yl)methyl]-10-methylpyrido[1,2-a]indol-6(7H)-one (2.06 g).

mp: 135°–136° C.

IR (Nujol): 1690, 1670, 1620 cm$^{-1}$

NMR (CDCl$_3$, δ): 0.8–1.0 (1H, m), 1.61 (3H, s), 1.65 (3H, s), 1.8–2.2 (1H, m), 2.7–3.4 (3H, m), 4.9–5.1 (1H, m), 5.5–5.6 (1H, m), 6.66 (1/2H, s), 6.71 (1/2H, s), 7.0–7.5 (18H, m), 8.3–8.5 (1H, m)

EXAMPLE 41

8,9-Dihydro-7-[(hydroxy)(2-methyl-1H-imidazol-4-yl)methyl]-10-methylpyrido[1,2-a]indol-6(7H)-one was prepared in a similar manner to that of Example 28.

mp: 210°–211° C.

IR (Nujol): 3200, 1660, 1630, 1575, 1530 cm$^{-1}$

NMR (DMSO-d$_6$, δ): 1.7–2.1 (2H, m), 2.13 (3H, s), 2.45 (3H, s), 2.6–2.8 (1H, m), 3.0–3.2 (2H, m), 3.33 (1H, br s), 5.27 (1H, d, J=4.85 Hz), 5.48 (1H, br s), 6.78 (1H, s), 7.2–7.3 (2H, m), 7.4–7.5 (1H, m), 8.3–8.4 (1H, m)

MS (m/e): 309 (M$^+$)

EXAMPLE 42

Acetic anhydride (1.31 g) was added to a solution of 8,9-dihydro-7-[(hydroxy)(2-methyl-1-trityl-1H-imidazol-4-yl)methyl]-10-methylpyrido[1,2-a]indol-6(7H)-one (1.42 g) in pyridine (20 ml). After being stirred at room temperature for 6 hours, the solution was evaporated in vacuo. The residue was diluted with chloroform, washed with 5% aqueous solution of sodium hydrogencarbonate and brine, and dried over anhydrous magnesium sulfate. After the solvent was evaporated in vacuo, the residue was subjected to column chromatography on silica gel (5% methanol-chloroform). The fractions containing the product were evaporated in vacuo and crystallized from n-hexane-ether to give 7-[(acetoxy)(2-methyl-1-trityl-1H-imidazol-4-yl)methyl]-8,9-dihydro-10-methyl-pyrido[1,2-a]indol-6(7H)-one (1.3 g).

mp: 183–188 (dec.)

IR (Nujol): 1730, 1685, 1625 cm$^{-1}$

NMR (DMSO-d$_6$, δ): 1.43 (3/2H, s), 1.52 (3/2H, s), 1.86 (3/2H, s), 2.02 (3/2H, s), 2.14 (3H, s), 1.9–2.3 (2H, m), 2.7–3.2 (2H, m), 3.31 (1H, s), 3.33 (1H, s), 6.4–6.6 (1H, m), 6.9–7.4 (18H, m), 8.1–8.4 (1H, m)

MS (m/e): 593 (M$^-$)

EXAMPLE 43

8,9-Dihydro-10-methyl-7-[(2-methyl-1-trityl-1H-imidazol-4-yl)methylene]pyrido[1,2-a]indol-6(7H)-one was prepared in a similar manner to that of Example 5.

mp: 232°–233° C. (dec.)

IR (Nujol): 1680, 1620, 1610 cm$^{-1}$

NMR (DMSO-d$_6$, δ): 1.60 (3H, s), 2.18 (3H, s), 2.9–3.1 (2H, m), 3.4–3.6 (2H, m), 7.0–7.6 (20H, m), 8.3–8.4 (1H, m)

MS (m/e): 533 (M$^-$)

EXAMPLE 44

8,9-Dihydro-10-methyl-7-[(2-methyl-1H-imidazol-4-yl)methyl]pyrido[1,2-a]indol-6(7H)-one hydrochloride was prepared in a similar manner to that of Example 31.

mp: >250° C.

IR (Nujol): 3260, 1680, 1630 cm$^{-1}$

NMR (DMSO-d$_6$, δ): 1.7–1.9 (1H, m), 2.0–2.2 (1H, m), 2.14 (3H, s), 2.56 (3H, s), 2.7–3.5 (6H, m), 7.2–7.3 (2H, m), 7.31 (1H, s), 7.4–7.5 (1H, m), 8.3–8.4 (1H, m), 14.39 (1H, br s)

MS (m/e): 293 (M$^+$)

EXAMPLE 45

To a solution of 8,9-dihydro-7-[(1H-imidazol-4yl)methyl]-10-methylpyrido[1,2-a]indol-6(7H)-one (1.4 g) in N,N-dimethylformamide (14 ml) at 5° C. was added sodium hydride (60% in mineral oil) (220 mg). After stirring for 1 hour at 5° C., methyl iodide (852 mg) in dimethylformamide (5 ml) was added dropwise at 5° C. for 10 minutes. The mixture was stirred at 5° C. for 1 hour and at 20° C. for 2 hours. After evaporation of the solvent, the residue was diluted with 5% methanol-chloroform. The organic layer was washed twice with brine, dried over anhydrous magnesium sulfate, and evaporated in vacuo. The obtained residue contained two products which showed close Rf values (0.5 and 0.4 respectively) by TLC (20% methanol-chloroform). Separation with silica gel column chromatography (5% methanol-chloroform) gave two fractions. The first eluted fraction, containing a mixture of two products, was concentrated. The crystalline residue was recrystallized from ethyl acetate to give 8,9-dihydro-10-methyl-7-[(1-methyl-1H-imidazol-4-yl)methyl]pyrido[1,2-a]indol-6(7H)-one (0.4 g).

mp: 99°–100° C.

IR (Nujol): 1685, 1675, 1615 cm$^{-1}$

NMR (CDCl$_3$, δ): 1.8–2.3 (2H, m), 2.15 (3H, s), 2.6–3.2 (4H, m), 3.33 (1H, dd, J=3.83, 13.71 Hz), 3.62 (3H, s), 6.73 (1H, s), 7.2–7.5 (4H, m)

MS (m/e): 293 (M$^-$)

The second elution was evaporated in vacuo to give 8,9-dihydro-10-methyl-7-[(1-methyl-1H-imidazol-5-yl)methyl]pyrido[1,2-a]indol-6(7H)-one (0.03 g).

mp: 117°–118° C.

IR (Nujol): 1688, 1668, 1620 cm$^{-1}$

NMR (DMSO-d$_6$, δ): 1.7–2.2 (2H, m), 2.14 (3H, s), 2.7–2.9 (2H, m), 3.0–3.3 (3H, m), 3.33 (3H, s), 6.72 (1H, s), 7.2–7.3 (2H, m), 7.4–7.4 (1H, m), 7.52 (1H, s), 8.3–8.4 (1H, m)

MS (m/e): 293 (M$^+$)

EXAMPLE 46

8,9-Dihydro-7-[(1,5-dimethyl-1H-imidazol-4-yl)methyl]-10-methylpyrido[1,2-a]indol-6(7H)-one and 8,9-dihydro-7-[(1,4-dimethyl-1H-imidazol-5-yl)methyl]-10-methylpyrido[1,2-a]indol-6(7H)-one were prepared in a similar manner to that of Example 45.

8,9-Dihydro-7[(1,5-dimethyl-1H-imidazol-4-yl)methyl]-10-methylpyrido[1,2-a]indol-6(7H)-one.

mp: 169°–170° C.

IR (Nujol): 1686, 1630, 1570 cm$^{-1}$

NMR (CDCl$_3$, δ): 1.81–1.97 (1H, m), 2.15 (3H, s), 2.19 (3H, s), 2.1–2.3 (1H, m), 2.6–2.8 (2H, m), 3.0–3.2 (2H, m), 3.36 (1H, q, J=4.23, 14.5 Hz), 3.51 (3H, s), 7.2–7.3 (2H, m), 7.33 (1H, s), 8.37–8.41 (1H, m), 8.4–8.5 (1H, m)

MS (m/e): 307 (M$^+$) 8,9-Dihydro-7-[(1,4-dimethyl-1H-imidazol-5-yl)methyl]-10-methylpyrido[1,2-a]indol-6(7H)-one.

mp: 193°–194° C.

IR (Nujol): 1688, 1636, 1570

NMR (CDCl$_3$, δ): 1.7–1.83 (1H, m), 2.0–2.15 (2H, m), 2.17 (6H, s), 2.6–2.8 (3H, m), 3.0–3.2 (1H, m), 3.4–3.6 (1H, m), 3.60 (3H, s), 7.26–7.32 (2H, m), 7.35 (1H, s), 7.38–7.43 (1H, m), 8.39–8.43 (1H, m)

MS (m/e): 307 (M$^+$)

EXAMPLE 47

To a solution of diisopropylamine (263 mg) in tetrahydrofuran (3 ml) at −70° C. under a nitrogen atmosphere was added 1.64M butyllithium in hexane (1.75 ml). After being stirred at the same temperature for 20 minutes, the mixture was treated with a solution of 8,9-dihydro-10-methyl-7-[(5-methyl-1-trityl-1H-imidazol-4-yl)methyl]pyrido[1,2-a]indol-6(7H)-one (1.07 g) in tetrahydrofuran (5 ml) over 15 minutes. The mixture was stirred at −65° C. for 30 minutes and at −25° C. for 40 minutes and a solution of methyl iodide (282 mg) in tetrahydrofuran (3 ml) was added dropwise at −65° C. over 10 minutes. After the mixture was stirred at −65° C. for 30 minutes and at −20° C. for 1 hour, it was diluted with water and neutralized with an aqueous solution of oxalic acid. The resultant mixture was extracted with ethyl acetate. The organic layer was washed with brine, dried over anhydrous magnesium sulfate, and evaporated in vacuo. Purification of the residue with silica gel column chromatography (5% ethyl acetate-chloroform) gave 8,9-dihydro-7,10-dimethyl-7-[(5-methyl-1-trityl-1H-imidazol-4-yl)methyl]pyrido[1,2-a]indol-6(7H)-one (0.73 g).

mp: 116°–118° C.

IR (Nujol): 1680, 1625, 1580 cm$^{-1}$

NMR (CDCl$_3$, δ): 1.30 (3H, s), 1.36 (3H, s), 1.9–2.1 (1H, m), 2.17 (3H, s), 2.3–2.5 (1H, m), 2.93 (2H, ABq,

J=14.3 Hz), 2.8-3.3 (2H, m), 7-7.4 (19H, m), 8.4-8.5 (1H, m)

MS (m/e): 549 (M+)

EXAMPLE 48

8,9-Dihydro-7,10-dimethyl-7-[(5-methyl-1H-imidazol-4-yl)methyl]pyrido[1,2-a]indol-6(7H)-one was prepared in a similar manner to that of Example 28.

mp: 163°-164° C.

IR (Nujol): 1680, 1625, 1585 cm$^{-1}$

NMR (CDCl$_3$, δ): 1.39 (3H, s), 1.9-2.1 (2H, m), 2.14 (3H, s), 2.19 (3H, s), 2.71 (1H, d, J=14.7 Hz), 2.8-3.3 (2H, m), 3.27 (1H, d, J=14.7 Hz), 7.2-7.5 (4H, m), 8.4-8.5 (1H, m)

MS (m/e): 307 (M+)

EXAMPLE 49

To a solution of diisopropylamine (1.44 ml) in tetrahydrofuran (5 ml) at −60° C. under a nitrogen atmosphere was added 1.64M butyllithium in hexane (6.3 ml). After being stirred at the same temperature for 30 minutes, the mixture was treated with a solution of 2-chloro-8,9-dihydro-10-methylpyrido[1,2-a]indol-6(7H)-one (2.0 g) in tetrahydrofuran (25 ml) over 10 minutes. The mixture was stirred at −70° C. for 20 minutes, and a solution of 5-methyl-1-trityl-1H-imidazol-4-carbaldehyde (3.32 g) in tetrahydroruran (45 ml) was added dropwise over 30 minutes. After the mixture was stirred at −70° C. for further 2 hours, it was diluted with water (70 ml) and dichloromethane (70 ml). After neutralization with hydrochloric acid, the organic layer was separated, washed with water twice and brine, dried over sodium sulfate, and evaporated in vacuo. The obtained oil was tritulated with dichloromethane and diisopropyl ether (1:5, V/V) to give colorless powder, which contains two diastereoisomers of 2-chloro-8,9-dihydro-7-[(hydroxy)(5-methyl-1-trityl-1H-imidazol-4-yl)methyl]-10-methylpyrido[1,2-a]indol-6(7H)-one (2.24 g).

IR (Nujol): 1705, 1615, 1590 cm$^{-1}$

EXAMPLE 50

A solution of the mixture of two diastereoisomers of 2-chloro-8,9-dihydro-7-[(hydroxy)(5-methyl-1-trityl-1H-imidazol-4-yl)methyl]-10-methylpyrido[1,2-a]indol-6(7H)-one (0.50 g) in acetic acid-water (5:2, 7 ml) was stirred at 60° C. for 2 hours. After evaporation of the solvent, the residue was partitioned between water and chloroform and neutralized with an aqueous sodium hydroxide, to give precipitates. The organic layer and the precipitates were combined and chromatographed on silica gel eluted by chloroform-methanol (0-10% V/V), to give two isomers of 2-chloro-8,9-dihydro-10-methyl-7[(hydroxy)(5-methyl-1H-imidazol-4-yl)methyl]pyrido[1,2-a]indol-6(7H)-one (0.037 g), respectively.

isomer A: (upper Rf on TLC (silica gel, chloroform-methanol 9:1 V/V)

mp: 193°-195° C.

IR (Nujol): 1660, 1630 cm$^{-1}$

NMR (DMSO-d$_6$, δ): 1.8-2.1 (2H, m), 2.10 (3H, s), 2.17 (3H, s), 2.6-3.2 (3H, m), 5.26 (2H, br s), 7.25 (1H, dd, J=2 Hz, J=9 Hz), 7.36 (1H, s), 7.52 (1H, d, J=2 Hz), 8.24 (1H, d, J=9 Hz), 11.70 (1H, br s)

MS (m/z): 343 (M+)

isomer B: (lower Rf on TLC)

mp: 185°-188° C.

IR (Nujol): 1680, 1620 cm$^{-1}$

NMR (DMSO-d$_6$, δ): 1.9-2.1 (2H, m), 2.13 (3H, s), 2.19 (3H, s), 2.6-3.3 (3H, m), 5.28 (1H, br s), 5.54 (1H, s), 7.28 (1H, dd, J=2 Hz, J=8.5 Hz), 7.45 (1H, s), 7.55 (1H, d, J=2 Hz), 8.32 (1H, d, J=8.5 Hz), 11.80 (1H, br s)

MS (m/z): 343 (M+)

EXAMPLE 51

To a solution of 2-chloro-8,9-dihydro-7-[(hydroxy)(5-methyl-1-trityl-1H-imidazol-4-yl)methyl]-10-methyl-pyrido[1,2-a]indol-6(7H)-one (1.64 g) in dichloromethane (32 ml) were added pyridine (0.83 ml) and acetic anhydride (0.53 ml). The solution was refluxed for 24 hours. After being cooled, the solution was washed with water twice and brine, dried over sodium sulfate, and evaporated, to give 7-[(acetoxy)(5-methyl-1-trityl-1H-imidazol-4-yl)methyl]-2-chloro-8,9-dihydro-10-methylpyrido[1,2-a]indol-6(7H)-one (1.49 g).

IR (Nujol): 1725, 1690, 1615 cm$^{-1}$

EXAMPLE 52

To a solution of 7-[(acetoxy)(5-methyl-1-trityl-1H-imidazol-4-yl)methyl]-2-chloro-8,9-dihydro-10-methyl-pyrido[1,2-a]indol-6(7H)-one (1.40 g) in toluene (15 ml) was added 1.8-diazabicyclo[5.4.0]undec-7-ene (0.37 ml), and the mixture was refluxed for 2 hours. After being cooled, the solution was washed with water and brine, dried over sodium sulfate, evaporated, and triturated in diisopropyl ether, to give 2-chloro-8,9-dihydro-10-methyl-7-[(5-methyl-1-trityl-1H-imidazol-4-yl)methylene]pyrido[1,2-a]indol-6(7H)-one (1.11 g).

mp: 224°-227° C.

IR (Nujol): 1685, 1620 cm$^{-1}$

NMR (CDCl$_3$, δ): 1.67 (3H, s), 2.17 (3H, s), 2.98 (2H, t, J=6.5 Hz), 3.66 (2H, t, J=6.5 Hz), 7.1-7.5 (19H, m), 7.73 (1H, s), 8.42 (1H, d, J=9 Hz)

EXAMPLE 53

To a solution of 2-chloro-8,9-dihydro-10-methyl-7-[(5-methyl-1-trityl-1H-imidazol-4-yl)methylene]-pyrido[1,2-a]indol-6(7H)-one (0.95 g) in acetic acid (47.5 ml) was added zinc powder (1.09 g) and the mixture was refluxed for 2.5 hours. The resulting precipitates were filtered off, and the filtrate was evaporated in vacuo. The residue was diluted in chloroform, washed with aqueous sodium bicarbonate, solution, water, and brine, dried over sodium sulfate, and chromatographed on silica gel eluted by chloroform-methanol (0-5% V/V), to give 2-chloro-8,9-dihydro-10-methyl-7-[(5-methyl-1H-imidazol-4-yl)methyl]pyrido[1,2-a]indol-6(7H)-one (0.50 g).

mp: 244°-246° C.

IR (Nujol): 1683, 1620 cm$^{-1}$

NMR (DMSO-d$_6$, δ): 1.7-2.1 (2H, m), 2.10 (3H, s), 2.12 (3H, s), 2.6-3.5 (5H, m), 7.28 (1H, dd, J=2 Hz, J=9 Hz), 7.41 (1H, s), 7.55 (1H, d, J=2 Hz), 8.30 (1H, d, J=9 Hz), 11.60 (1H, br s)

MS (m/z): 327 (M+)

EXAMPLE 54

8,9-Dihydro-2,10-dimethyl-7-[(hydroxy)(5-methyl-1-trityl-1H-imidazol-4-yl)methyl]pyrido[1,2-a]indol-6(7H)-one was prepared in a similar manner to that of Example 49.

IR (Nujol): 1675, 1615 cm$^{-1}$

EXAMPLE 55

8,9-Dihydro-2,10-dimethyl-7-[(5-methyl-1H-imidazol-4-yl)methyl]pyrido[1,2-a]indol-6(7H)-one was prepared in a similar manner to that of Example 56.
mp: 255°–258° C.
IR (Nujol): 1677, 1620 cm$^{-1}$
NMR (CDCl$_3$, MeOH-d$_4$, δ): 1.6–2.3 (2H, m), 2.13 (3H, s), 2.17 (3H, s), 2.43 (3H, s), 2.5–3.1 (5H, m), 7.08 (1H, d, J=9 Hz), 7.19 (1H, s), 7.39 (1H, s), 8.28 (1H, d, J=9 Hz)
M/S (m/z): 307 (M$^+$)

EXAMPLE 56

To a solution of 8,9-dihydro-7-[(hydroxy)(5-methyl-1-trityl-1H-imidazol-4-yl)methyl]-10-methylpyrido[1,2-a]indol-6(7H)-one (4.6 g) in acetic acid (92 ml) were added 10% palladium on carbon (2.3 g) and ammonium formate (7.89 g), and the mixture was refluxed gently for 3 hours. After being cooled, the catalyst was filtered off. The filtrate was evaporated, and diluted with water (50 ml) and diisopropyl ether (50 ml). Aqueous sodium hydroxide was added to neutralized the solution. Resulted precipitates were collected, and washed with water and diisopropyl ether successively, to give 8,9-dihydro-10-methyl-7-[(5-methyl-1H-imidazol-4-yl)methyl]pyrido[1,2-a]indol-6(7H)-one (1.87 g).
mp: 225°–227° C.
IR (Nujol): 1615, 1690 cm$^{-1}$
NMR (DMSO-d$_6$, δ): 1.5–2.2 (2H, m), 2.12 (6H, s), 2.5–3.3 (5H, m), 7.2–7.3 (2H, m), 7.39 (1H, s), 7.45 (1H, m), 8.34 (1H, m)
MS (m/z): 293 (M$^+$)

EXAMPLE 57

7-[(Acetoxy)(5-methyl-1-trityl-1H-imidazol-4-yl)methyl]-8,9-dihydro-10-methylpyrido[1,2-a]indol-6(7H)-one was converted into 8,9-dihydro-10-methyl-7-[(5-methyl-1H-imidazol-4-yl)methyl]pyrido[1,2-a]indol-6(7H)-one in a similar manner to that of Example 56.
IR (Nujol): 1615, 1690 cm$^{-1}$

EXAMPLE 58

8,9-Dihydro-10-methyl-7-[(5-methyl-1-trityl-1H-imidazol-4-yl)methylene]pyrido[1,2-a]indol-6(7H)-one was converted into 8,9-dihydro-10-methyl-7-[(5-methyl-1H-imidazol-4-yl)methyl]pyrido[1,2-a]indol-6(7H)-one in a similar manner to that of Example 67.
IR (Nujol): 1615, 1690 cm$^{-1}$

EXAMPLE 59

(+)-Di-p-toluoyl-D-tartaric acid (45.50 g) and 8,9-dihydro-10-methyl-7-[(5-methyl-1H-imidazol-4-yl)methyl]pyrido[1,2-a]indol-6(7H)-one (34.55 g) were dissolved in a mixture of chloroform-methanol (3:7, 2.35 l) at 70° C. The solution was allowed to stand at 5° C. for 7 days to give crystals (31.0 g). The crystals (30.8 g) were dissolved in N,N-dimethylformamide (69 ml) at 80° C. The resulting solution was diluted successively with chloroform (69 ml) and methanol (323 ml) and then allowed to stand at 5° C. for 5 days to give the (+)-di-p-toluoyl-D-tartaric acid salt (17.75 g).
mp: 178°–180° C.
The crystals were dissolved in N,N-dimethylformamide (53 ml) at 80° C. The solution was diluted with 10% methanol-chloroform (180 ml) and water (270 ml). The mixture was treated with 2N aqueous sodium hydroxide solution (14 ml) to neutralize the salt. The organic layer was washed with water three times, dried over anhydrous magnesium sulfate, and evaporated in vacuo to give crystalline (+)-8,9-dihydro-10-methyl-7-[(5-methyl-1H-imidazol-4-yl)methyl]pyrido[1,2-a]indol-6(7H)-one (7.1 g) with [α]$_D^{25}$=+63 (C=1.0, 10% methanol-chloroform).

The crystals were dissolved in hot methanol (160 ml) containing 12N hydrochloric acid (4.5 ml). After evaporation of the solvent to 70 ml, the solution was diluted with ether and allowed to stand at 5° C. for 2 days. The crystals were collected and dried to give (+)-8,9-dihydro-10-methyl-7-[(5-methyl-1H-imidazol-4-yl)methyl]pyrido[1,2-a]indol-6(7H)-one hydrochloride (7.3 g).
mp: >250° C.
IR (Nujol): 1700, 1635, 1520, 1310 cm$^{-1}$
NMR (DMSO-d$_6$, δ): 1.75–2.20 (2H, m), 2.14 (3H, s), 2.26 (3H, s), 2.73–3.40 (5H, m), 7.26 (2H, m), 7.49 (1H, m), 8.32 (1H, m), 8.98 (1H, s), 14.55 (2H, br s)
[α]$_D^{20}$=+14.1 (C=2, methanol)

EXAMPLE 60

10-Allyl-8,9-dihydro-7-[(hydroxy)(5-methyl-1-trityl-1H-imidazol-4-yl)methyl]pyrido[1,2-a]indol-6(7H)-one was prepared in a similar manner to that of Example 64 as an amorphous powder.
IR (Nujol): 1685, 1615, 1225 cm$^{-1}$

EXAMPLE 61

7-[(Acetoxy)(5-methyl-1-trityl-1H-imidazol-4-yl)methyl]-10-allyl-8,9-dihydropyrido[1,2-a]indol-6(7H)-one was prepared in a similar manner to that of Example 65 as an amorphous powder.
IR (Nujol): 1730, 1685, 1610 cm$^{-1}$

EXAMPLE 62

10-Allyl-8,9-dihydro-7-[(5-methyl-1-trityl-1H-imidazol-4-yl)methylene]pyrido[1,2-a]indol-6(7H)-one was prepared in a similar manner to that of Example 66.
mp: 211°–214° C.
IR (Nujol): 1685, 1620, 1350, 1140 cm$^{-1}$
NMR (DMSO-d$_6$, δ): 1.61 (3H, s), 3.00 (2H, m), 3.43 (2H, d, J=7 Hz), 3.57 (2H, m), 5.00–5.15 (2H, m), 5.95 (1H, m), 7.10–7.59 (20H, m), 8.37 (1H, m)

EXAMPLE 63

A mixture of 10-allyl-8,9-dihydro-7-[(5-methyl-1-trityl-1H-imidazol-4-yl)methylene]pyrido[1,2-a]indol-6(7H)-one and zinc powder (2.0 g) in acetic acid (30 ml) was stirred vigorously at 100° C. for 2 hours. Zinc powder (1.5 g) was added and the mixture was heated for further 1 hour. After being cooled to room temperature, the insoluble material was filtered and washed with acetic acid. After evaporation of the solvent, the residue was diluted with water and washed twice with toluene. The toluene layer was extracted with 0.5N hydrochloric acid. The combined aqueous layers were neutralized with aqueous sodium bicarbonate solution and extracted three times with chloroform. The chloroform layer was washed with water twice and brine, dried over anhydrous magnesium sulfate, and evaporated in vacuo. Chromatography (silica gel, 5% methanol-chloroform) of the residue, followed by recrystallization from methanol-chloroform-hexane, gave 10-allyl-8,9-dihydro-7-[(5-methyl-1H-imidazol-4-yl)methyl]pyrido[1,2-a]indol-6(7H)-one (0.63 g).
mp: 215°–217° C.
IR (Nujol): 1690, 1635, 1615, 1295 cm$^{-1}$
NMR (DMSO-d$_6$, δ): 1.80 (1H, m), 2.00 (1H, m), 2.10 (3H, s), 2.60–2.80 (2H, m), 2.95–3.15 (3H, m), 3.38 (2H, d, J=6 Hz), 4.99–5.12 (2H, m), 5.90 (1H, m), 7.24 (2H, m), 7.40 (1H, s), 7.50 (1H, m), 8.35 (1H, m), 11.60 (1H, br s)

EXAMPLE 64

To a solution of diisopropylamine (1.85 g) in tetrahydrofuran (15 ml) at −70° C. under a nitrogen atmosphere was added 1.49M butyllithium in hexane (11.5 ml). After being stirred at the same temperature for 35 minutes, the mixture was treated with a solution of 10-ethyl-8,9-dihydropyrido[1,2-a]indol-6(7H)-one (3.2 g) in tetrahydrofuran (20 ml) over 5 minutes. The mixture was stirred at −70° C. for 40 minutes, and a solution of 5-methyl-1-trityl-1H-imidazol-4-carbaldehyde (5.81 g) in tetrahydrofuran (65 ml) was added dropwise over 30 minutes. After the mixture was stirred at −70° C. for 2 hours and then at room temperature for 1 hour, it was diluted with chilled water, neutralized with aqueous oxalic acid solution, and extracted with methylene chloride three times. The organic layer was washed with water and brine, dried over anhydrous magnesium sulfate, and evaporated in vacuo. The oil obtained was purified by silica gel column chromatography (1% methanol-chloroform) to give 10-ethyl-8,9-dihydro-7-[(hydroxy)(5-methyl-1-trityl-1H-imidazol-4-yl)methyl]-pyrido[1,2-a]indol-6(7H)-one (6.8 g) as an amorphous powder. The product was a mixture of two diastereoisomers.

IR (Nujol): 1685, 1615, 1225 cm$^{-1}$

EXAMPLE 65

Acetic anhydride (2.0 ml) was added to a solution of 10-ethyl-8,9-dihydro-7-[(hydroxy)(5-methyl-1-trityl-1H-imidazol-4-yl)methyl]pyrido[1,2-a]indol-6(7H)-one (2.15 g) in pyridine (10 ml). After being stirred at room temperature for 20 hours, the solution was evaporated in vacuo. The residue was dissolved in toluene (30 ml) and the solution was evaporated in vacuo to remove pyridine and acetic anhydride. This operation was repeated further three times to give 7-[(acetoxy)(5-methyl-1-trityl-1H-imidazol-4-yl)methyl]-10-ethyl-8,9-dihydropyrido[1,2-a]indol-6(7H)-one as an amorphous powder. This crude product was used in the next reaction without further purification.

IR (Nujol): 1730, 1690, 1615, 1230 cm$^{-1}$

EXAMPLE 66

To a solution of 7-[(acetoxy)(5-methyl-1-trityl-1H-imidazol-4-yl)methyl]-10-ethyl-8,9-dihydropyrido[1,2-a]indol-6(7H)-one (2.06 g) in toluene (30 ml) at room temperature was added 1,8-diazabicyclo[5.4.0]undec-7-ene (1.2 ml). After being stirred at 75° C. for 3 hours, the solution was diluted with chilled water. The organic layer separated was washed with aqueous oxalic acid solution, water, and brine, dried over anhydrous sodium sulfate, and evaporated in vacuo. The residue was triturated with methanol and filtered to give 10-ethyl-8,9-dihydro-7-[(5-methyl-1-trityl-1H-imidazol-4-yl)methylene]pyrido[1,2-a]indol-6(7H)-one (1.41 g).

mp: 217°–220° C.
IR (Nujol): 1680, 1620, 1340 cm$^{-1}$
NMR (DMSO-d$_6$, δ): 1.18 (3H, t, J=7.5 Hz), 1.61 (3H, s), 2.67 (2H, m), 2.98 (2H, m), 3.58 (2H, m), 7.10–7.60 (20H, m), 8.37 (1H, m)

EXAMPLE 67

A mixture of 10-ethyl-8,9-dihydro-7-[(5-methyl-1-trityl-1H-imidazol-4-yl)methylene]pyrido[1,2-a]indol-6(7H)-one (1.0 g), 10% palladium on carbon (0.25 g), and ammonium formate (0.5 g) in acetic acid (14 ml) was stirred at 90° C. for 1 hour and 45 minutes and cooled to room temperature. After filtration of the catalyst, the filtrate was evaporated in vacuo and the residue was suspended in 0.5N hydrochloric acid. The aqueous layer was washed twice with toluene, made basic with aqueous sodium bicarbonate solution, and extracted three times with chloroform. The chloroform layer was washed with water twice and brine, dried over anhydrous magnesium sulfate, and evaporated to give crystals. Recrystallization from chloroform-methanol gave 10-ethyl-8,9-dihydro-7-[(5-methyl-1H-imidazol-4-yl)methyl]pyrido[1,2-a]indol-6(7H)-one (0.319 g).

mp: 222°–224° C.
IR (Nujol): 1690, 1618, 1300, 1185 cm$^{-1}$
NMR (DMSO-d$_6$, δ): 1.15 (3H, t, J=7.5 Hz), 1.75 (1H, m), 1.97 (1H, m), 2.10 (3H, s), 2.50–2.84 (4H, m), 2.95–3.19 (3H, m), 7.25 (2H, m), 7.41 (1H, s), 7.51 (1H, m), 8.35 (1H, m), 11.62 (1H, br s)

EXAMPLE 68

To a solution of diisopropylamine (395 mg) in tetrahydrofuran (5 ml) at −70° C. under a nitrogen atmosphere was added 1.64M butyllithium in hexane (2.62 ml). After being stirred at the same temperature for 20 minutes, the mixture was treated with a solution of 8,9-dihydro-10-methyl-7-[(5-methyl-1-trityl-1H-imidazol-4-yl)methyl]pyrido[1,2-a]indol-6(7H)-one (1.61 g) in tetrahydrofuran (5 ml) over 15 minutes. The mixture was stirred at −65° C. for 30 minutes and at −30°~−40° C. for 30 minutes and a solution of allyl bromide (363 mg) in tetrahydrofuran (5 ml) was added dropwise at −65° C. over 10 minutes. After the mixture was stirred at −65° C. for 1 hour, at −20° C. for 1 hour and at ambient temperature for 1 hour. The resultant mixture was washed with water (10 ml×2) and brine, dried over anhydrous magnesium sulfate and evaporated in vacuo. Purification of the residue with silica gel column chromatography (5% ethyl acetate-chloroform) gave 7-allyl-8,9-dihydro-10-methyl-7-[(5-methyl-1-trityl-1H-imidazol-4-yl)methyl]pyrido[1,2-a]indol-6(7H)-one (1.15 g).

mp: 83°–85° C.
IR (Nujol): 1670, 1610 cm$^{-1}$
NMR (CDCl$_3$, δ): 1.32 (3H, s), 2.22 (3H, s), 2.0–2.4 (4H, m), 2.7–3.2 (4H, m), 5.0–5.2 (2H, m), 5.7–6.0 (1H, m), 7.0–7.5 (19H, m), 8.3–8.5 (1H, m)

EXAMPLE 69

7-Allyl-8,9-dihydro-10-methyl-7-[(5-methyl-1H-imidazol-4-yl)methyl]pyrido[1,2-a]indol-6(7H)-one was prepared in a similar manner to that of Example 71.

mp: 209°–210° C.
IR (Nujol): 1680, 1640, 1590 cm$^{-1}$
NMR (DMSO-d$_6$, δ): 1.8–2.4 (4H, m), 2.03 (3H, s), 2.13 (3H, s), 2.6–3.1 (4H, m), 5.0–5.2 (2H, m), 4.7–6.0 (1H, m) 7.2–7.5 (3H, m), 7.38 (1H, s), 8.2–8.4 (1H, m), 11.6 (1H, br s)
MS (m/e): 333 (M+)

EXAMPLE 70

7-Ethyl-8,9-dihydro-10-methyl-7-[(5-methyl-1-trityl-1H-imidazol-4-yl)methyl]pyrido[1,2-a]indol-6(7H)-one was prepared in a similar manner to that of Example 68.

mp: 83°–98° C.
IR (Nujol): 1680, 1630 cm$^{-1}$

NMR (CDCl$_3$, δ): 0.96 (3H, t, J=7.38 Hz), 1.33 (3H, s), 1.4–1.7 (1H, m), 1.9–2.4 (4H, m), 2.2 (3H, s), 2.83, 3.04 (2H, ABq, J=14.3 Hz), 2.8–3.1 (1H, m), 7.0–7.5 (19H, m), 8.4–8.5 (1H, m)

EXAMPLE 71

A solution of 7-ethyl-8,9-dihydro-10-methyl-7-[(5-methyl-1-trityl-1H-imidazol-4-yl)methyl]pyrido[1,2-a]indol-6(7H)-one (0.45 g) in acetic acid (10 ml) and water (2.5 ml) was stirred at 60° C. for 2 hours. After evaporation of the solvent, the residue was diluted with ether (10 ml) and an aqueous solution of sodium hydrogencarbonate (10 ml). The resultant mixture was stirred for 30 minutes at ambient temperature. The insoluble material was collected, washed with water and ether, and dried to give crystalline 7-ethyl-8,9-dihydro-10-methyl-7-[(5-methyl-1H-imidazol-4-yl)methyl]-pyrido[1,2-a]indol-6(7H)-one (0.20 g).

mp: 202°–204° C.
IR (Nujol): 1685, 1625, 1600 cm$^{-1}$
NMR (DMSO-d$_6$, δ): 0.87 (3H, t, J=7.8 Hz), 1.4–1.6 (1H, m), 1.7–2.2 (3H, m), 2.07 (3H, s), 2.13 (3H, s), 2.71, 2.90 (2H, ABq, J=14.3 Hz), 2.9–3.2 (2H, m), 7.2–7.5 (3H, m), 7.36 (1H, s), 8.3–8.4 (1H, m), 11.61 (1H, s)

EXAMPLE 72

8,9-Dihydro-7-hydroxymethyl-10-methyl-7-[(5-methyl-1-trityl-1H-imidazol-4-yl)methyl]pyrido[1,2-a]indol-6(7H)-one was prepared in a similar manner to that of Example 68 except for using paraformaldehyde in place of allyl bromide.

mp: 85°–88° C.
IR (Nujol): 1680, 1620 cm$^{-1}$
NMR (CDCl$_3$, δ): 1.26 (3H, s), 2.0–2.1 (2H, m), 2.16 (3H, s), 2.85–3.19 (2H, ABq, J=14.8 Hz), 3.00 (2H, t, J=6.3 Hz), 3.71, 4.07 (2H, ABq, J=11.8 Hz), 7.1–7.5 (19H, m), 8.3–8.4 (1H, m)

EXAMPLE 73

A solution of 8,9-dihydro-7-hydroxymethyl-10-methyl-7-[(5-methyl-1-trityl-1H-imidazol-4-yl)methyl]-pyrido[1,2-a]indol-6(7H)-one (0.6 g) in acetic acid (15 ml) and water (3 ml) was stirred at 60° C. for an hour. After evaporation of the solvent, the residue was diluted with chloroform, washed with an aqueous solution of sodium hydrogencarbonate and brine, dried over anhydrous magnesium sulfate, and evaporated in vacuo. The residue was dissolved with ethyl acetate and treated with hydrogen chloride in ether to give 8,9-dihydro-7-hydroxymethyl-10-methyl-7-[(5-methyl-1H-imidazol-4-yl)methyl]pyrido[1,2-a]indol-6(7H)-one hydrochloride (0.18 g).

mp: 230°–260° C. (dec.)
IR (Nujol): 3350, 1680, 1620 cm$^{-1}$
NMR (DMSO-d$_6$, δ): 1.8–2.3 (2H, m), 2.14 (6H, m), 2.9–3.5 (6H, m), 3.56, 3.77 (2H, ABq, J=10.7 Hz), 7.2–7.5 (3H, m), 8.2–8.3 (1H, m), 8.91 (1H, s), 14.2 (1H, br s)

EXAMPLE 74

A mixture of 8,9-dihydro-10-methyl-7-(dimethylaminomethyl)pyrido[1,2-a]indol-6(7H)-one (0.65 g), 2-methylimidazole (0.76 g), 2N hydrochloric acid (1.27 ml), and isopropyl alcohol (4 ml) was heated at 100° C. for 3 hours and 15 minutes. After evaporation of the solvent, the residue obtained was dissolved in methylene chloride. The methylene chloride solution was washed with water and brine, dried over anhydrous magnesium sulfate and evaporated in vacuo. Purification with neutral alumina column chromatography (0.5% methanol-methylene chloride), followed by recrystallization with ethyl acetate-hexane, gave 8,9-dihydro-10-methyl-7-[(2-methyl-1H-imidazol-1-yl)methyl]-pyrido[1,2-a]indol-6(7H)-one (0.40 g).

mp: 120°–121° C.
IR (Nujol): 1665, 1615, 1520, 1280 cm$^{-1}$
NMR (DMSO-d$_6$, δ): 1.60–1.90 (2H, m), 2.10 (3H, s), 2.30 (3H, s), 2.66–3.40 (3H, m), 4.13 (1H, dd, J=8, 15 Hz), 4.50 (1H, dd, J=5, 15 Hz), 6.73 (1H, s), 7.03 (1H, s), 7.10–7.50 (3H, m), 8.30 (1H, m)

EXAMPLE 75

A mixture of 8,9-dihydro-10-methyl-7-methylenepyrido[1,2-a]indol-6(7H)-one (142 mg), 2-methylimidazole (180 mg), isopropyl alcohol (1 ml) and water (0.4 ml) was heated at 100° C. for 3 hours. The reaction mixture was purified by a procedure analogous to that of Example 74 to give 8,9-dihydro-10-methyl-7-[(2-methyl-1H-imidazol-1-yl)methyl]pyrido[1,2-a]indol-6(7H)-one (60 mg).

mp: 120°–121° C.

EXAMPLE 76

8,9-Dihydro-7-[(hydroxy)[5-methyl-1-(N,N-dimethylsulfamoyl)-1H-imidazol-4-yl]methyl]-10-methyl-pyrido[1,2-a]indol-6(7H)-one was prepared in a similar manner to that of Example 64 as an amorphous powder.

IR (Nujol): 1685, 1620, 1170 cm$^{-1}$

EXAMPLE 77

7-[(Acetoxy)[5-methyl-1-(N,N-dimethylsulfamoyl)-1H-imidazol-4-yl]methyl]-8,9-dihydro-10-methyl-pyrido[1,2-a]indol-6(7H)-one was prepared in a similar manner to that of Example 65 as an amorphous powder.

IR (CHCl$_3$): 1730, 1695, 1630, 1170 cm$^{-1}$

EXAMPLE 78

8,9-Dihydro-10-methyl-7-[[5-methyl-1-(N,N-dimethylsulfamoyl)-1H-imidazol-4-yl]methylene]pyrido[1,2-a]indol-6(7H)-one was prepared in a similar manner to that of Example 66.

mp: 200°–205° C.
IR (Nujol): 1680, 1625, 1350, 1160 cm$^{-1}$
NMR (DMSO-d$_6$, δ): 2.19 (3H, s), 2.52 (3H, s), 2.93 (6H, s), 2.98 (2H, t, J=7 Hz), 3.51 (2H, t, J=7 Hz), 7.29 (2H, m), 7.51 (1H, m), 7.61 (1H, s), 8.27 (1H, s), 8.39 (1H, m)

EXAMPLE 79

A mixture of 8,9-dihydro-10-methyl-7-[[5-methyl-1-(N,N-dimethylsulfamoyl)-1H-imidazol-4-yl]methylene]pyrido[1,2-a]indol-6(7H)-one (0.83 g), ammonium formate (0.75 g), and 10% palladium on carbon (0.1 g) in acetic acid (10 ml) was stirred at 90° C. for 3 hours and cooled to room temperature. After filtration of the catalyst, the filtrate was evaporated in vacuo. The residue was made basic with aqueous sodium bicarbonate solution and extracted with methylene chloride three times. The organic layer was washed with water and brine, dried over anhydrous magnesium sulfate, and evaporated in vacuo. Chromatography of the obtained oil (silica gel, 0.5% methanol-chloroform) gave three fractions. The first eluted fractions contained the starting material (166 mg). The second eluted fractions contained 8,9-dihydro-10-methyl-7-[[5-methyl-1-(N,N-dimethylsulfamoyl)-1H-imidazol-4-yl]methyl]-pyrido[1,2-a]indol-6(7H)-one (130 mg) as an oil.

IR (CHCl₃): 1685, 1625, 1165, 970 cm⁻¹

NMR (CDCl₃, δ): 1.85 (1H, m), 2.16 (3H, s), 2.16 (1H, m), 2.36 (3H, s), 2.70–2.90 (2H, m), 2.88 (6H, s), 3.02–3.13 (2H, m), 3.35 (1H, dd, J=4.5, 15 Hz), 7.28 (2H, m), 7.41 (1H, m), 7.85 (1H, s), 8.44 (1H, m)

The third eluted fractions gave 8,9-dihydro-10-methyl-7-[(5-methyl-1H-imidazol-4-yl)methyl]pyrido[1,2-a]indol-6(7H)-one (90 mg) which was recrystallized from methanol to give crystals (40 mg).

mp: 224°–226° C.

IR (Nujol): 1690, 1620, 1325, 1300 cm⁻¹

EXAMPLE 80

A mixture of 8,9-dihydro-10-methyl-7-[[5-methyl-1-(N,N-dimethylsulfamoyl)-1H-imidazol-4-yl]methyl]-pyrido[1,2-a]indol-6(7H)-one (93 mg), 3N hydrochloric acid (3 ml), and ethanol (2 ml) was heated at 90° C. for 2.5 hours. After evaporation of the solvent, the residue was neutralized with aqueous sodium bicarbonate solution and extracted three times with chloroform. The organic layer was washed with water and brine, dried over anhydrous magnesium sulfate, and evaporated in vacuo. Chromatography of the residue (solvent, 4% methanol-chloroform) gave 8,9-dihydro-10-methyl-7-[(5-methyl-1H-imidazol-4-yl)methyl]pyrido[1,2-a]indol-6(7H)-one (42 mg).

mp: 224°–226° C.

IR (Nujol): 1690, 1620, 1325, 1300 cm⁻¹

PREPARATION 5

To a suspension of 5-methyl-1H-imidazole-4-carbaldehyde (20 g) in N,N-dimethylformamide (100 ml) was added triethylamine (20.5 g) and p-toluenesulfonyl chloride (38 g). The mixture was stirred under ice-cooling for two hours. The reaction mixture was diluted with water (600 ml) and separated organic layer was filtered. The residue obtained was suspended in methanol (100 ml). After being stirred at ambient temperature for two hours, the mixture was cooled and filtered to give 5-methyl-1-tosyl-1H-imidazole-4-carbaldehyde (40.3 g).

NMR (CDCl₃, δ): 2.47 (3H, s), 2.61 (3H, s), 7.42 (2H, d, J=8 Hz), 7.87 (2H, d, J=8 Hz), 8.14 (1H, s), 9.94 (1H, s)

MS (m/e): 264 (M⁺)

EXAMPLE 81

8,9-Dihydro-7-[(hydroxy) (5-methyl-1-tosyl-1H-imidazol-4-yl)methyl]-10-methylpyrido[1,2-a]indol-6(7H)-one was prepared in a similar manner to that of Example 64.

NMR (DMSO-d₆, δ): 2.11 (3H, s), 2.29 (3H, s), 1.90–2.10 (2H, m), 2.39 (3H, s), 2.70 (1H, m), 3.05 (1H, m), 3.20 (1H, m), 5.22 (1H, t, J=5 Hz), 5.35 (1H, d, J=5 Hz), 7.2 (2H, m), 7.4 (1H, m), 7.45 (2H, d, J=8 Hz), 7.85 (2H, d, J=8 Hz), 8,17 (1H, m), 8.2 (1H, m)

MS (m/e): 463 (M⁺)

EXAMPLE 82

7-[(Acetoxy) (5-methyl-1-tosyl-1H-imidazol-4-yl)methyl]-8,9-dihydro-10-methylpyrido[1,2-a]indol-6(7H)-one was prepared in a similar manner to that of Example 65.

NMR (DMSO-d₆, δ): 2.00 (3H, s), 1.90–2.10 (2H, m), 2.11 (3H, s), 2.28 (3H, s), 2.39 (3H, s), 2.80 (1H, m), 3.00 (1H, m), 3.50 (1H, m), 6.29 (1H, d, J=7 Hz), 7.20–7.30 (2H, m), 7.40 (1H, m), 7.40 (2H, d, J=8 Hz), 7.87 (2H, d, J=8 Hz), 8.10 (1H, m), 8.27 (1H, s)

MS (m/e): 445 (M⁺-OCOCH₃)

EXAMPLE 83

8,9-Dihydro-10-methyl-7-[(5-methyl-1-tosyl-1H-imidazol-4-yl)methylene]pyrido[1,2-a]indol-6(7H)-one was prepared in a similar manner to that of Example 66.

NMR (DMSO-d₆, δ): 2.17 (3H, s), 2.50 (3H, s), 2.51 (3H, s), 2.95 (2H, t, J=7 Hz), 3.45 (2H, t, J=7 Hz), 7.20–7.30 (2H, m), 7.52 (2H, d, J=8 Hz), 7.49 (1H, s), 8.00 (2H, d, J=8 Hz), 8.30 (1H, m), 8.54 (1H, s)

MS (m/e): 445 (M⁺)

EXAMPLE 84

To a solution of 8,9-dihydro-10-methyl-7-[(5-methyl-1-tosyl-1H-imidazol-4-yl)methylene]pyrido[1,2-a]indol-6(7H)-one (1.0 g) in the mixture of tetrahydrofuran (10 ml) and methanol (10 ml) was added 2N-sodium hydroxide. The mixture was heated at 80° C. for 5 hours. After being cooled, the reaction mixture was neutralized with acetic acid, and added water (40 ml). The precipitates were filtered to give 8,9-dihydro-10-methyl-7-[(5-methyl-1H-imidazol-4-yl)methylene]-pyrido[1,2-a]indol-6(7H)-one (0.5 g).

NMR (DMSO-d₆, δ): 2.18 (3H, s), 2.36 (3H, s), 2.95 (2H, t, J=6.0 Hz), 3.58 (2H, t, J=6.0 Hz), 7.64 (1H, s), 7.74 (1H, s), 7.20–7.30 (2H, m), 7.50–7.60 (1H, m), 8.30–8.40 (1H, m), 12.34 (1H, s)

MS (m/e): 2.91 (M⁺)

EXAMPLE 85

8,9-Dihydro-10-methyl-7-[(5-methyl-1H-imidazol-4-yl)methyl]pyrido[1,2-a]indol-6(7H)-one was prepared in a similar manner to that of Example 39.

NMR (DMSO-d₆, δ): 1.60–2.10 (2H, m), 2.13 (3H, s), 2.18 (3H, s), 2.70–3.30 (5H, m), 7.20–7.30 (3H, m), 7.44–7.51 (1H, m), 8.21 (1H, s), 8.28–8.34 (1H, m)

EXAMPLE 86

(a) A mixture of 8,9-dihydro-7,10-dimethyl-7-[(5-methyl-1-trityl-1H-imidazol-4-yl)methyl]pyrido[1,2-a]indol-6(7H)-one (3.78 g), aqueous 3N sodium hydroxide solution (10 ml), ethanol (10 ml) and dioxane (5 ml) was heated at 90° C. for 30 hours. After evaporation of the solvent, the residue was diluted with water, neutralized with aqueous oxalic acid solution, and extracted three times with chloroform. The chloroform layer was washed with water and brine, dried over anhydrous sodium sulfate, and evaporated in vacuo to give 2-methyl-4-(3-methylindol-2-yl)-2-[(5-methyl-1-trityl-1H-imidazol-4-yl)methyl]butyric acid (3.3 g) as an amorphous powder. The product was used in the next reaction without purification.

IR (Nujol): 3300–2100, 1680, 1490 cm⁻¹

(b) To a solution of 2-methyl-4-(3-methylindol-2-yl)-2-[(5-methyl-1-trityl-1H-imidazol-4-yl)methyl]butyric acid (2.55 g) and triethylamine (0.71 ml) in tetrahydrofuran (30 ml) at −20° C. was added a solution of ethyl chloroformate (0.54 g) in tetrahydrofuran (2 ml). After being stirred at the same temperature for 17 minutes, a solution of 2(S)-pyrrolidinemethanol (1.14 g) in tetrahydrofuran (3 ml) was added to the solution. The solution was stirred at −10° C. for 2 hours and then at room temperature for one hour. The reaction mixture was diluted with chilled water, neutralized with aqueous oxalic acid solution, and extracted three times with chloroform. The chloroform layer was washed with water and brine, dried over anhydrous sodium sulfate, and evaporated in vacuo. Silica gel column chromatography (1.5% methanol-chloroform) of the residue gave a mixture of diastereomers of (2S)-2-[1-[2-methyl-4-(3-methylindol-2-yl)-2-[(5-methyl-1-trityl-1H-imidazol-4-yl)methyl]-butyryl]pyrrolidine]methanol (2.0 g). The mixture was separated by silica gel column chromatography using ethyl acetate-hexane (1:1) as eluent. Evaporation of the first eluted fraction gave one isomer of (2S)-2-[1-[2-methyl-4-(3-methylindol-2-yl)-2-[(5-methyl-1-trityl-1H-imidazol-4-yl)methyl]butyryl]pyrrolidine]methanol (0.48 g), which was designated as the isomer A, as an amorphous powder.

IR (Nujol): 3200, 1600, 1230 cm$^{-1}$

NMR (CDCl$_3$, δ): 1.28 (3H, s), 1.10–1.50 (4H, m), 1.45 (3H, s), 1.70–2.10 (3H, m), 2.17 (3H, s), 2.52 (1H, d, J=14.6 Hz), 2.75 (2H, t, J=8 Hz), 3.12 (1H, d, J=14.6 Hz), 3.32 (1H, d, J=11.6 Hz), 3.75 (1H, m), 3.89 (1H, m), 4.24 (1H, m), 4.38 (1H, d, J=11.6 Hz), 6.99–7.46 (20H, m)

The second eluted fraction gave the other isomer of (2S)-2-[1-[2-methyl-4-(3-methylindol-2-yl)-2-[(5-methyl-1-trityl-1H-imidazol-4-yl)methyl]butyryl]pyrrolidine]methanol (0.54 g), which was designated as the isomer B, as an amorphous powder.

IR (Nujol): 3250, 1600, 1240 cm$^{-1}$

NMR (CDCl$_3$, δ): 1.08 (3H, s), 1.20–1.50 (4H, m), 1.38 (3H, s), 1.70–2.00 (2H, m), 2.22 (3H, s), 2.10–2.40 (2H, m), 2.70–2.88 (2H, m), 3.16–3.27 (2H, m), 3.60–3.83 (2H, m), 4.17 (1H, m), 4.32 (1H, d, J=11 Hz), 7.00–7.48 (20H, m)

(c) A mixture of the isomer B of (2S)-2-[1-[2-methyl-4-(3-methylindol-2-yl)-2-[(5-methyl-1-trityl-1H-imidazol-4-yl)methyl]butyryl]pyrrolidine]methanol (0.52 g), 3N-hydrochloric acid (20 ml) and toluene (10 ml) was refluxed for 4 hours. After evaporation of the solvent, the residue was made basic with aqueous sodium bicarbonate solution and extracted three times with chloroform. The chloroform layer was washed with water and brine, dried over anhydrous magnesium sulfate, and evaporated in vacuo. The residue was chromatographed on silica gel column (5% methanol-chloroform) to give (+)-8,9-dihydro-7,10-dimethyl-7-[(5-methyl-1H-imidazol-4-yl)methyl]pyrido[1,2-a]indol-6(7H)-one (175 mg) with $[\alpha]_D^{25}$ = +204° (C=1.0, 10% methanol-chloroform) as a powder. The product was treated with hydrogen chloride in methanol and recrystallized from methanol-ether to give (+)-8,9-dihydro-7,10-dimethyl-7-[(5-methyl-1H-imiazol-4-yl)methyl]-pyrido[1,2-a]indol-6(7H)-one hydrochloride (90 mg).

mp: >250° C.

IR (Nujol): 1700, 1640, 1625 cm$^{-1}$

NMR (DMSO-d$_6$, δ): 1.29 (3H, s), 1.94 (2H, m), 2.15 (3H, s), 2.18 (3H, s), 3.00 (2H, m), 7.26 (2H, m), 7.50 (1H, m), 8.30 (1H, m), 8.92 (1H, s), 14.16 (1H, s)

(d) (−)-8,9-Dihydro-7,10-dimethyl-7-[(5-methyl-1H-imidazol-4-yl)methyl]pyrido[1,2-a]indol-6(7H)-one hydrochloride was prepared from the isomer A of (2S)-2-[1-[2-methyl-4-(3-methylindol-2-yl)-2-[(5-methyl-1-trityl-1H-imidazol-4-yl)methyl]butyryl]pyrrolidine]methanol in a similar manner to that of Example 86(c).

mp: >250° C.

IR (Nujol): 1700, 1640, 1620, 1520 cm$^{-1}$

NMR (DMSO-d$_6$, δ): 1.29 (3H, s), 2.00 (2H, m), 2.15 (3H, s), 2.18 (3H, s), 3.00 (2H, m), 7.26 (2H, m), 7.50 (1H, m), 8.30 (1H, m), 8.94 (1H, s), 14.29 (1H, s)

The intermediate, (−)-8,9-dihydro-7,10-dimethyl-7-[(5-methyl-1H-imidazol-4-yl)methyl]pyrido[1,2-a]indol-6-(7H)-one showed the $[\alpha]_D^{25}$ value of −202.5° (C=0.98, 10% methanol-chloroform).

EXAMPLE 87

To a suspension of 8,9-dihydro-7-[(5-methyl-1H-imidazol-4-yl)methyl]pyrido[1,2-a]indol-6(7H)-one (500 mg) in N,N-dimethylformamide (5 ml) at room temperature was added sodium hydride (60% in mineral oil, 79 mg). After stirring at room temperature for 10 minutes and then at 5° C. for 5 minutes, the solution was treated with a solution of benzyl chloride (249 mg) in N,N-dimethylformamide (1 ml) at 5° C. The mixture was stirred at 5° C. for 10 minutes and then at room temperature for 2 hours. The reaction mixture was diluted with chilled water and extracted twice with chloroform. The chloroform layer was washed with water and brine, dried over anhydrous magnesium sulfate, and evaporated in vacuo. The oil obtained was purified by silica gel column chromatography (1% methanol-chloroform) to give 7-[(1-benzyl-5-methyl-1H-imidazol-4-yl)methyl]-8,9-dihydropyrido[1,2-a]indol-6(7H)-one (468 mg).

mp: 130°–140° C.

IR (Nujol): 1695, 1595, 1570, 1495 cm$^{-1}$

NMR (CDCl$_3$, δ): 1.80–2.30 (2H, m), 2.07 (3H, s), 2.70–3.30 (4H, m), 3.40 (1H, dd, J=2.0, 14.4 Hz), 5.03 (2H, s), 6.28 (1H, s), 7.04 (2H, m), 7.20–7.45 (7H, m), 8.46 (1H, m)

EXAMPLE 88

To a mixture of aqueous 50% dimethylamine solution (0.20 ml), aqueous 35% formaldehyde solution (0.20 ml), and acetic acid (4 ml) at 15° C. was added 8,9-dihydro-7-[(5-methyl-1H-imidazol-4-yl)methyl]pyrido[1,2-a]indol-6(7H)-one (418 mg). The mixture was heated at 60° C. for 24 hours. After evaporation of the solvent, the residue was dissolved in water, made basic with aqueous 3N sodium hydroxide solution, and extracted three times with chloroform. The chloroform layer was washed with water and brine, dried over anhydrous sodium sulfate, and evaporated in vacuo. The oil was purified by silica gel column chromatography (20% methanol-chloroform) to give 8,9-dihydro-10-[(dimethylamino)methyl]-7-[(5-methyl-1H-imidazol-4-yl)methyl]pyrido[1,2-a]indol-6(7H)-one (240 mg).

mp: 195°–197° C.

IR (Nujol): 1695, 1610 cm$^{-1}$

NMR (DMSO-d$_6$, δ): 1.60–2.20 (2H, m), 2.10 (3H, s), 2.16 (6H, s), 2.60–2.90 (2H, m), 3.00–3.50 (3H, m), 3.45 (2H, s), 7.25 (2H, m), 7.41 (1H, s), 7.62 (1H, m), 8.35 (1H, m)

EXAMPLE 89

To a solution of 7-[(1-benzyl-5-methyl-1H-imidazol-4-yl)methyl]-8,9-dihydropyrido[1,2-a]indol-6(7H)-one (451 mg) in acetic acid (2.5 ml) at 10° C. were added successively aqueous 50% dimethylamine solution (0.17 ml) and aqueous 35% formaldehyde solution (0.16 ml). The mixture was heated at 60° C. for 16 hours. After evaporation of the solvent, the residue was dissolved in water, made basic with aqueous 3N sodium hydroxide solution, and extracted twice with chloroform. The chloroform layer was washed with water and brine, dried over anhydrous sodium sulfate, and evaporated in vacuo. The residue was purified by silica gel column chromatography (methanol-chloroform) to give 7-[(1-benzyl-5-methyl-1H-imidazol-4-yl)methyl]-10-[(dimethylamino)methyl]-8,9-dihydropyrido[1,2-a]indol-6(7H)-one (233 mg) as an oil.

IR (Film): 1695, 1615, 1495 cm$^{-1}$

NMR (CDCl$_3$, δ): 1.80-2.20 (2H, m), 2.07 (3H, s), 2.26 (6H, s), 2.72-2.91 (2H, m), 3.06-3.23 (2H, m), 3.40 (1H, dd, J=4.4, 14.6 Hz), 3.48 (2H, s), 5.03 (2H, s), 7.05 (2H, m), 7.28 (5H, m), 7.45 (1H, s), 7.60 (1H, m), 8.47 (1H, m)

EXAMPLE 90

A mixture of 8,9-dihydro-10-[(dimethylamino)methyl]-7-[(5-methyl-1H-imidazol-4-yl)methyl]pyrido[1,2-a]indol-6(7H)-one (224 mg), ammonium formate (500 mg), 10% palladium on carbon (210 mg), water (1 ml), ethanol (2 ml) and tetrahydrofuran (1 ml) was heated at 75° C. for 45 minutes and then cooled. Ammonium formate (300 mg), 10% palladium on carbon (100 mg), water (1 ml), and ethanol (2 ml) were added successively to the reaction mixture. Heating at 75° C. was continued for further 1 hour. After cooling, the reaction mixture was filtered and the filtrate was evaporated in vacuo. The residue was diluted with water and extracted three times with chloroform. The chloroform layer was washed with water and brine, dried over anhydrous magnesium sulfate, and evaporated in vacuo. Silica gel column chromatography of the residue (5% methanol-chloroform) gave 8,9-dihydro-10-methyl-7-[(5-methyl-1H-imidazol-4-yl)methyl]pyrido[1,2-a]indol-6(7H)-one (118 mg).

IR (Nujol): 1690, 1615 cm$^{-1}$

EXAMPLE 91

A mixture of 7-[(1-benzyl-5-methyl-1H-imidazol-4-yl)methyl]-10-[(dimethylamino)methyl]-8,9-dihydropyrido-[1,2-a]indol-6(7H)-one (215 mg), ammonium formate (318 mg), 10% palladium on carbon (107 mg), water (1 ml), ethanol (2 ml), and tetrahydrofuran (1 ml) was heated at 75° C. for 40 minutes and then cooled. Ammonium formate (300 mg), 10% palladium on carbon (110 mg), water (1 ml), and ethanol (2 ml) were added successively to the reaction mixture. Heating at 75° C. was continued for further 1 hour 20 minutes. After cooling, the reaction mixture was filtered and the residue was washed with 10% methanol-chloroform. The filtrate was evaporated in vacuo. The residue was diluted with water and extracted three times with 10% methanol-chloroform. The organic layer was washed with water and brine, dried over anhydrous magnesium sulfte, and evaporated in vacuo. Silica gel column chromatography of the residue using 5% methanol-chloroform as eluent gave 8,9-dihydro-10-methyl-7-[(5-methyl-1H-imidazol-4-yl)methyl]pyrido[1,2-a]indol-6(7H)-one (108 mg).

IR (Nujol): 1690, 1615 cm$^{-1}$

EXAMPLE 92

To a solution of 7-allyl-8,9-dihydro-10-methyl-7-[(5-methyl-1H-imidazol-4-yl)methyl]pyrido[1,2-a]indol-6(7H)-one (250 mg) in a mixture of acetic acid (10 ml) and methanol (10 ml) was added 10% palladium on carbon (50 mg). The mixture was hydrogenated at an atmospheric pressure for 2 hours. After filtration of the catalyst, the filtrate was evaporated in vacuo. The residue was dissolved in a mixture of ethyl acetate (5 ml) and 2N-hydrochloric acid. After the mixture was stirred for 30 minutes, the precipitates were collected and washed with ethyl acetate to give 8,9-dihydro-10-methyl-7-[(5-methyl-1H-imidazol-4-yl)methyl]-7-propylpyrido[1,2-a]-indol-6(7H)-one hydrochloride.

mp: >270° C.

IR (Nujol): 1675, 1635, 1620 cm$^{-1}$

NMR (DMSO-d$_6$, δ): 0.87 (3H, t, J=6.82 Hz), 1.2-2.2 (6H, m), 2.9-3.1 (2H, m), 3.12 (2H, ABq, J=14.93 Hz), 7.2-7.3 (2H, m), 7.4-7.5 (1H, m), 8.2-8.4 (1H, m), 8.95 (1H, s)

MS (m/e): 335 (M+)

EXAMPLE 93

A mixture of 8,9-dihydro-10-ethyl-7-[(5-methyl-1H-imidazol-4-yl)methyl]pyrido[1,2-a]indol-6-(7H)-one (0.84 g), trityl chloride (1.0 g) and triethylamine (515 mg) in N,N-dimethylformamide (10 ml) was stirred at room temperature for 18 hours. The reaction mixture was diluted with chilled water and extracted twice with ethyl acetate. The organic layer was washed with water and brine, dried over anhydrous magnesium sulfate, and evaporated in vacuo. Purification of the residue with silica gel column chromatography (2% methanol-chloroform) gave 8,9-dihydro-10-ethyl-7-[(5-methyl-1-trityl-1H-imidazol-4-yl)methyl]pyrido[1,2-a]indol-6(7H)-one (690 mg).

mp: 78°-82° C.

IR (Nujol): 1690, 1630 cm$^{-1}$

NMR (DMSO-d$_6$, δ): 1.15 (3H, t, J=7.38 Hz), 1.33 (3H, s), 1.7-2.1 (2H, m), 2.5-3.2 (7H, m), 7.0-7.6 (20H, m), 8.3-8.4 (1H, m)

MS (m/e): 549 (M+)

EXAMPLE 94

To a solution of diisopropylamine (202.4 mg) in tetrahydrofuran (5 ml) at −50° C. under nitrogen atmosphere was added 1.64M-butyllithium in hexane (1.23 ml). After being stirred at −60°∼−70° C. for 30 minutes, the mixture was treated with a solution of 8,9-dihydro-10-ethyl-7-[(5-methyl-1-trityl-1H-imidazol-4-yl)methyl]pyrido[1,2-a]-indol-6(7H)-one (549 mg) in tetrahydrofuran (10 ml) over 20 minutes. The mixture was stirred at −60°∼−70° C. stirred for 60 minutes and a solution of methyl iodide (213 mg) in tetrahydrofuran (1 ml) was added dropwise at −60° C. over 10 minutes. After the mixture was stirred at −65° C. for 30 minutes and at −20° C. for 1 hour, it was diluted with water and extracted twice with ethyl acetate. The organic layer was washed with water and brine, dried over anhydrous magnesium sulfate, and evaporated in vacuo to give 8,9-dihydro-10-ethyl-7-methyl-7-[(5-methyl-1-trityl-1H-imidazol-4-yl)methyl]pyrido[1,2-a]indol-6(7H)-one, which was dissolved with 80% aqueous acetic acid (6 ml) and stirred at 60° C. for 2 hours. After evaporation of the solvent, the residue was diluted with water, neutralized with an aqueous sodium bicarbonate solution, and extracted twice with 10%-methanol-chloroform. The organic layer was washed with brine, dried over anhydrous magnesium sulfate and evaporated in vacuo. The residue was purified by silica gel column chromatography (5% methanol-chloroform). The obtained 8,9-dihydro-10-ethyl-7-methyl-7-[(5-methyl-1H-imidazol-4-yl)methyl]pyrido[1,2-a]indol-6(7H)-one was dissolved in 12N-hydrogenchloride in ethanol (1 ml) and evaporated in vacuo. Tritulation of the residue with ether gave 8,9-dihydro-10-ethyl-7-methyl-7-[(5-methyl-1H-imidazol-4-yl)methyl]-pyrido[1,2-a]indol-6(7H)-one hydrochloride (202.56 mg).

mp: 214°-217° C.

IR (Nujol): 1710, 1640, 1610 cm$^{-1}$

NMR (DMSO-d$_6$, δ): 1.17 (3H, t, J=7.37 Hz), 1.29 (3H, s), 1.8-2.2 (2H, m), 2.19 (3H, s), 2.60 (2H, q,

J=7.37 Hz), 2.9-3.4 (4H, m), 7.2-7.3 (2H, m), 7.5-7.6 (1H, m), 8.3-8.4 (1H, m), 8.96 (1H, s), 14.3 (1H, br s)

EXAMPLE 95

(+)-Di-p-Toluoyl-D-tartaric acid (3.86 g) and 8,9-dihydro-7-[(5-methyl-1H-imidazol-4-yl)methyl]-pyrido[1,2-a]indol-6(7H)-one (2.79 g) were dissolved in a mixture of chloroform-methanol (2:8, 84 ml) at 60° C. The solution was allowed to stand at 5° C. for 20 hours to give crystals (2.17 g). The crystals separated were dissolved in a mixture of chloroform-methanol (2:8, 32 ml) at 60° C. The solution was allowed to stand at 5° C. for 3 days to give the (+)-Di-toluoyl-D-tartaric acid salt (1.66 g). Small amount of crystals (147 mg) was suspended in aqueous sodium bicarbonate solution. The mixture was extracted twice with 10% methanol-chloroform. The organic layer was washed aqueous sodium bicarbonate solution and water, dried over anhydrous sodium sulfate, and evaporated in vacuo. The residue was purified by silica gel column chromatography (5% methanol-chloroform) to give (+)-8,9-dihydro-7-[(5-methyl-1H-imidazol-4-yl)methyl]pyrido[1,2-a]indol-6(7H)-one (61 mg) as crystals with $[\alpha]_D^{25}$ of +50.6° (C=1.22, 10% methanol-chloroform).

mp: 198°-202° C.

IR (Nujol): 2600, 1695, 1620, 1590, 1570 cm$^{-1}$

EXAMPLE 96

A mixture of 8,9-dihydro-7-[(5-methyl-1-trityl-1H-imidazol-4-yl)methylene]pyrido[1,2-a]indol-6(7H)-one (21.28 g), acetic acid (500 ml), and water (80 ml) was stirred at 80° C. for 1 hour and 10 minutes. After evaporation of the solvent, the residue was diluted with water, neutralized with aqueous sodium bicarbonate solution and 3N aqueous sodium hydroxide solution, and extracted with chloroform to give precipitates. The precipitates were collected, washed with water and chloroform, and dried to give 8,9-dihydro-7-[(5-methyl-1H-imidazol-4-yl)methylene]pyrido[1,2-a]indol-6(7H)-one (5.8 g). The chloroform layer separated was washed with water and brine, dried over anhydrous magnesium sulfate, and evaporated to 50 ml. The chloroform solution was diluted with toluene and allowed to stand at room temperature overnight. The crystals were collected and washed with toluene to give a second crop of 8,9-dihydro-7-[(5-methyl-1H-imidazol-4-yl)methylene]pyrido[1,2-a]indol-6(7H)-one (5.2 g).

mp: 214°-215° C.

IR (Nujol): 1690, 1640, 1610, 1580 cm$^{-1}$

NMR (DMSO-d$_6$, δ): 2.37 (3H, s), 3.01 (2H, t, J=7.1 Hz), 3.56 (2H, t, J=7.1 Hz), 6.46 (1H, s), 7.26 (2H, m), 7.51 (1H, m), 7.67 (1H, s), 7.74 (1H, s), 8.40 (1H, m), 12.36 (1H, s)

EXAMPLE 97

To a mixture of 8,9-dihydro-7-[(5-methyl-1H-imidazol-4-yl)methylene]pyrido[1,2-a]indol-6(7H)-one (10.9 g), ammonium formate (17.2 g), ethanol (130 ml), and tetrahydrofuran (110 ml) was added a suspension of 10% palladium on carbon (3.3 g) in water (30 ml). The mixture was heated at 60° C. for 2 hours and then cooled. After filtration of the catalyst, the filtrate was evaporated in vacuo. The residue was dissolved in 10% methanol-chloroform. The organic layer was washed successively with aqueous sodium bicarbonate solution, water, and brine, dried over anhydrous magnesium sulfate, and evaporated in vacuo. The crystalline residue was recrystallized from chloroform-hexane to give 8,9-dihydro-7-[(5-methyl-1H-imidazol-4-yl)methyl]-pyrido[1,2-a]indol-6(7H)-one (9.85 g).

mp: 195°-197° C.

IR (Nujol): 1700, 1600, 1580 cm$^{-1}$

NMR (DMSO-d$_6$, δ): 1.70-2.10 (2H, m), 2.11 (3H, s), 2.65-3.21 (5H, m), 6.41 (1H, s), 7.22 (2H, m), 7.41 (1H, s), 7.50 (1H, m), 8.35 (1H, m), 11.63 (1H, s)

EXAMPLE 98

A suspension of 10-ethyl-8,9-dihydro-7-[(5-methyl-1H-imidazol-4-yl)methyl]pyrido[1,2-a]indol-6(7H)one (285 mg) in methanol (20 ml) was treated with 12N hydrochloric acid (0.2 ml) and heated at 60° C. After concentration of the solution under reduced pressure to 3 ml, the solution was diluted with ether (6 ml) and allowed to stand at room temperature. The crystals were collected and washed with ether to give 10-ethyl-8,9-dihydro-7-[(5-methyl-1H-imidazol-4-yl)methyl]-pyrido[1,2-a]indol-6(7H)one hydrochloride (273 mg).

mp: >260° C.

IR (Nujol): 1702, 1640, 1625 cm$^{-1}$

NMR (DMSO-d$_6$, δ): 1.16 (3H, t, J=7.4 Hz), 1.70-2.10 (2H, m), 2.26 (3H, s), 2.63 (2H, q, J=7.4 Hz), 2.60-3.40 (5H, m), 7.27 (2H, m), 7.54 (1H, s), 8.33 (1H, m), 8.96 (1H, s), 14.46 (2H, br s)

EXAMPLE 99

10-Allyl-8,9-dihydro-7-[(5-methyl-1H-imidazol-4-yl)methyl]pyrido[1,2-a]indol-6(7H)one hydrochloride was prepared in a similar manner to that of Example 98.

mp: 208°-216° C.

IR (Nujol): 1700, 1640, 1620 cm$^{-1}$

NMR (DMSO-d$_6$, δ): 1.65-2.10 (2H, m), 2.27 (3H, s), 2.70-3.40 (7H, m), 4.99-5.14 (2H, m), 5.80-6.02 (1H, m), 7.25 (2H, m), 7.51 (1H, m), 8.34 (1H, m), 8.97 (1H, s), 14.55 (2H, br s)

What we claim is:

1. A compound of formula:

wherein
- $R^1$ is hydrogen, lower alkyl, lower alkenyl or N,N-di(lower)alkylaminomethyl,
- $R^2$ is hydrogen, lower alkyl or halogen,
- $R^3$ is imidazolyl or pyridyl, each of which may have substituent(s) selected from lower alkyl and iminoprotective group which is selected from mono-, di- or triphenyl(lower)alkyl, N,N-di(lower)alkylsulfamoyl, lower alkanesulfonyl and tosyl, and
- $R^4$ is hydrogen, lower alkyl, lower alkenyl or hydroxy(lower)alkyl and $R^5$ is hydrogen, hydroxy or lower alkanoyloxy, or
- $R^4$ and $R^5$ are linked together to form an additional bond, or a pharmaceutically acceptable salt thereof.

2. A compound of claim 1, wherein
$R^3$ is imidazolyl which may have one to three substitutent(s) selected from lower alkyl and iminoprotective group which is selected from mono-, di- or triphenyl(lower)alkyl, N,N-di(lower)alkylsulfamoyl, lower alkanesulfonyl and tosyl.

3. A compound of claim 2, wherein $R^3$ is 2-lower alkyl-1H-imidazol-1-yl, 1H-imidazol-2-yl, 1-ar(lower)alkyl-1H-imidazol-2-yl, 1-ar(lower)alkyl-5-lower alkyl-1H-imidazol-4-yl, 5-lower alkyl-1H-imidazol-4-yl, 1-ar(lower)alkyl-1H-imidazol-4-yl, 1H-imidazol-4-yl, 2-lower alkyl-5-lower alkyl-1H-imidazol-4-yl, 1-ar(lower)alkyl-2-lower alkyl-1H-imidazol-4-yl, 2-lower alkyl-1H-imidazol-4-yl, 1-lower alkyl-1H-imidazol-4-yl, 1-lower alkyl-5-lower alkyl-1H-imidazol-4-yl, 1-di(lower)alkylaminosulfonyl-5-lower alkyl-1H-imidazol-4-yl, 1-lower alkyl-1H-imidazol-5-yl or 1-lower alkyl-4-lower alkyl-1H-imidazol-5-yl.

4. A compound of claim 3, wherein
 $R^1$ is lower alkyl,
 $R^2$ is hydrogen,
 $R^3$ is 1-mono or di or triphenyl(lower)alkyl-5-lower alkyl-1H-imidazol-4-yl, 5-lower alkyl-1H-imidazol-4-yl or 1-di(lower)alkylaminosulfonyl-5-lower alkyl-1H-imidazol-4-yl, and
 $R^4$ is hydrogen and $R^5$ is hydrogen, hydroxy or lower alkanoyloxy, or
 $R^4$ and $R^5$ are linked together to form an additional bond.

5. A compound of claim 4, wherein
 $R^3$ is 5-lower alkyl-1H-imidazol-4-yl, and
 $R^4$ and $R^5$ are each hydrogen.

6. A compound of claim 5, which is 8,9-dihydro-10-methyl-7-[(5-methyl-1H-imidazol-4-yl)methyl]pyrido[1,2-a]indol-6(7H)-one or its acid addition salt.

7. A compound of claim 6, which is (+)8,9-dihydro-10-methyl-7-[(5-methyl-1H-imidazol-4-yl)methyl]pyrido[1,2-a]indol-6(7H)-one or its hydrochloride or its maleate.

8. A 5-HT antagonist pharmaceutical composition comprising an effective amount of a compound of claim 1 or pharmaceutically acceptable salt thereof in association with a pharmaceutically acceptable, substantially non-toxic carrier or excipient.

9. A method for treating or preventing nausea or vomiting, which comprises administering an effective amount of a compound of claim 1 or pharmaceutically acceptable salt thereof to a human being or animal.

* * * * *